United States Patent [19]
Liu et al.

[11] Patent Number: 5,354,847
[45] Date of Patent: Oct. 11, 1994

[54] CHIMERIC ANTIBODY WITH SPECIFICITY TO HUMAN TUMOR ANTIGEN

[75] Inventors: Alvin Y. Liu, Santa Monica; Randy R. Robinson, Los Angeles, both of Calif.; Karl E. Hellstrom; Ingegred Hellstrom, both of Seattle, Wash.

[73] Assignee: Bristol-Myers Squibb Company, New York, N.Y.

[21] Appl. No.: 759,707

[22] Filed: Sep. 12, 1991

Related U.S. Application Data

[63] Continuation of Ser. No. 614,954, Nov. 15, 1990, abandoned, which is a continuation of Ser. No. 923,244, Oct. 27, 1986, abandoned.

[51] Int. Cl.$^5$ .................... C07K 15/28; C12N 5/20; C12N 15/13
[52] U.S. Cl. .............. 530/387.3; 435/172.2; 435/172.3; 435/240.27; 530/387.7
[58] Field of Search .............. 435/7.23, 7.9, 172.2, 435/172.3, 240.27; 436/548, 813; 530/387.3, 387.7, 391.1, 391.3, 391.7; 424/1.1, 9, 85.8, 85.91; 935/15

[56] References Cited

U.S. PATENT DOCUMENTS

| | | | |
|---|---|---|---|
| 4,468,464 | 8/1984 | Cohen et al. | 935/68 |
| 4,486,538 | 12/1984 | Bogoch et al. | |
| 4,550,756 | 3/1987 | Old et al. | |
| 4,708,862 | 11/1987 | Baldwin et al. | |
| 4,816,567 | 3/1989 | Cabilly | 530/387 |
| 4,906,562 | 3/1990 | Hellstrom et al. | 435/7.23 |
| 5,091,178 | 2/1992 | Hellstrom et al. | 424/85.8 |

FOREIGN PATENT DOCUMENTS

| | | |
|---|---|---|
| 0120694 | 10/1984 | European Pat. Off. |
| 0125023 | 11/1984 | European Pat. Off. |
| 171496 | 2/1985 | European Pat. Off. |
| 0173494 | 3/1986 | European Pat. Off. |
| 0184187 | 6/1986 | European Pat. Off. |
| 8303971 | 11/1983 | PCT Int'l Appl. |
| 8601533 | 3/1986 | PCT Int'l Appl. |
| WO86/03838 | 7/1986 | PCT Int'l Appl. |
| 87/02776 | 5/1987 | PCT Int'l Appl. |

OTHER PUBLICATIONS

M. Bruggemann et al, *Jour. Exp. Med.*, 166, 1351–1361, 1987.
I. M. Roitt, *Essential Immunology*, Blackwell Scientific Pub., 1984, pp. 165–166.
K. E. Hellstrom et al, in Baldwin et al. (Eds.) *Monoclonal Antibodies for Cancer Detection and Therapy*, Academic Press, New York, 1985, pp. 34–36.
M. Nose et al, *Proc. Natl. Acad. Sci USA*, 80, 6632–6636, 1983.
Z. Steplewski et al, *Proc. Natl Acad Sci USA*, 85, 4852–4856, 1988.
Reilly et al., 1984, J. Immunol. 133:471–475.
Marx, 1985, Science 229:455–456.
Hellstrom et al., *Cancer Research* 46:3917–3923 (Aug. 1986).
Hellstrom et al., *Proc. Natl. Acad. Sci. USA*, 83:7059–7063 (Sep. 1986).
Morrison et al. *Proc. Nat'l Acad. Sci.* (USA) 81:6851–5 (1984).
Boulianne, G. L., *Nature* 312:643–6 (1986).
Neuberger et al., *Nature* 314:268–70 (1985).
Neuberger et al., *Nature* 312:604–8 (1984).
Williams et al., *Genes* 43:319 (1986).
Takeda et al., *Nature* 314:452–4 (1985).
Cabilly et al., *Proc. Nat'l. Acad. Sci* (USA) 81:3273–7 (1984).
Wood et al., *Nature* 314:446 (1985).
Alexander et al., *Proc. Nat'l. Acad. Sci.* (USA) 79:3260–4 (1982).

(List continued on next page.)

*Primary Examiner*—David Saunders
*Attorney, Agent, or Firm*—Pennie & Edmonds

[57] ABSTRACT

A chimeric antibody with human constant region and murine variable region, having specificity to a human tumor antigen, methods of production, and uses. In particular, the present invention relates to a chimeric antibody specific for a human tumor antigen L6 and which mediates a potent antibody dependent cellular cytotoxicity against the tumor target cells.

4 Claims, 12 Drawing Sheets

OTHER PUBLICATIONS

Dolby et al., *Proc. Nat'l. Acad. Sci.* 77:6027–31 (1980).
Seno et al., *Nucleic Acid Research,* 11:719–26 (1983).
Kurokawa et al., *Nucleic Acid Research* 11:3077:85 (1983).
Liu et al., *Proc. Nat'l Acad. Sci.(USA)* 81:5369–73 (1984).
Tsujimoto et al., *Nucleic Acid Res.,* 12:8407–14 (1984).
Tan et al., *J. Immunol.* 135:3564–7 (1985).
Jones et al., *Nature,* 321:522–4 (1986).
Sun et al., *Hybridoma,* 5:Suppl. 1, 517 (1986).
Sahagan et al., *J. Immunol.,* 137:1066–74 (1986).
Morrison, S. L., *Science,* 229:1207–7 (1985) review.
Oi et al., *Biotechniques* 4:214–21 (1986) review.

Ig heavy chain J-C region human heavy chain J regions                                J | CH1

JH1   GCTGAATACTTCCAGCACTGGGGCCAGGGCACCCTGGTCACCGTCTCCTCAG.
JH2   CTACTGGTACTTCGATCTCTGGGGCCGTGGCACCCTGGTCACTGTCTCCTCAG
JH3       ATGCTTTTGATGTCTGGGGCCAAGGGACAATGGTCACCGTCTCTTCAG
JH4       ACTACTTTGACTACTGGGGCCAAGGAACCCTGGTCACCGTCTCCTCAG
JH5       ACACTGGTTCGACTCCTGGGGCCAAGGAACCCTGGTCACCGTCTCCTCAG
JH6   AT(TAC)₅GGTATGGACGTCTGGGGGCAAGGGACCACGGTCACCGTCTCCTCAG
Consensus       TCGACCTCTGGGGCCAAGGAACCCTGGTCACCGTCTCCTCAG mouse heavy chain J regions                                J | CH1

JH1   TACTGGTACTTCGATGTCTGGGGCGCAGGGACCACGGTCACCGTCTCCTCAG
JH2        TACTTTGACTACTGGGGCCAAGGCACCACTCTCACAGTCTCCTCAG
JH3        CCTGGTTTGCTTACTGGGGCCAAGGGACTCTGGTCACTGTCTCTGCAG
JH4   TACTATGCTATGGACTACTGGGGTCAAGGAACCTCAGTCACCGTCTCCTCAG
Consensus       TTTGACTACTGGGGCCAAGGGACCACGGTCACCGTCTCCTCAG Ig light chain J-C region human Kappa J region                                J | C JK1   GGACGTTCGGCCAAGGGACCAAGGTGGAAATCAAAC
JK2   ACACTTTTGGCCAGGGGACCAAGCTGGAGATCAAAC
JK3   TCACTTTCGGCCCTGGGACCAAAGTGGATATCAAAC
JK4   TCACTTTCGGCGGAGGGACCAAGGTGGAGATCAAAC
JK5   TCACCTTCGGCCAAGGGACACGACTGGAGATTAAAC
Consensus  TTCGGCCAAGGGACCAAGGTGGAGATCAAAC mouse Kappa J region                                J | C JK1   TGGACGTTCGGTGGAGGCACCAAGCTGGAAATCAAAC
JK2   TACACGTTCGGAGGGGGGACCAAGCTGGAAATAAAAC
JK3   TTCACATTCAGTGATGGGACCAGACTGGAAATAAAAC
JK4   TTCACGTTCGGCTCGGGGACAAAGTTGGAAATAAAAC
JK5   CTCACGTTCGGTGCTGGGACCAAGCTGGAGCTGAAAC
Consensus  TTCGGTGGGGGGACCAAGCTGGAAATAAAAC

UIG[MJK]           3'TGGTTCGACCTTTATTTTG 5'

FIG.2A human Lambda pseudo J region       J | C

JPSL1  CACATGTTTGGCAGCAAGACCCAGCCCACTGTCTTAG mouse Lambda J region              J | C JL1       TGGGTGTTCGGTGGAGGAACCAAACTGACTGTCCTAG
JL2       TATGTTTTCGGCGGTGGAACCAAGGTCACTGTCCTAG
JL3       TTTATTTTCGGCAGTGGAACCAAGGTCACTGTCCTAG
Consensus TTCGGCGGTGGAACCAAGGTCACTGTCCTAG

FIG.2B mouse heavy chain J segments

```
JH1    TACTGGTACTTCGATGTCTGGGGCGCAGGGACCAC GGTCACC GTCTCCTCA
JH2         TACTTTGACTACTGGGGCCAAGGCACCAC TCTCACA GTCTCCTCA
JH3          CCTGGTTTGCTTACTGGGGCCAAGGGACTCT GGTCACT GTCTCTGCA
JH4    TACTATGCTATGGACTACTGGGGTCAAGGAACCTC AGTCACC GTCTCCTCA
``` consensus primer: UIGH       AGGGACCAC GGTCACC GTCTC
                                     Bst EII mouse k light chain J segments

```
JK1         TGGACGTTCGGTGGAGGCACC AAGCTG GAAATCAAA
JK2         TACACGTTCGGAGGGGGGACC AAGCTG GAAATAAAA
JK4         TTCACGTTCGGCTCGGGGACA AAGTTG GAAATAAAA
JK5         CTCACGTTCGGTGCTGGGACC AAGCTG GAGCTGAAA
``` consensus primer: UIG$_K$       GGGACC AAGCTT GAG
                                 Hind III

FIG.3 pGMH 6 Human C$_\gamma$1 constant domain module

JH
G GTC ACC GTC TCT TCA|GCC TCC ACC AAG GGC CCA TCG GTC TTC –

Bst EII                                  Apa I pGML 60 Human C$_K$ constant domain module
                         J$_K$4
GAT CAT CTC CCT CTC ACT TTC GGC GGA GGG ACC AAG GTG GAG ATG AAA|–
                                     ——————C-T—— J$_K$Hind III
                                         Hind III

FIG.4

```
                        BamHI                                                    MET Asp Trp Leu Trp Asn Leu
L6 VH         GG ATC CCC CCC CCC CCC CAG TTT GTC TTA AGG CAC CAC TGA GCC ATG GAT TGG CTG TGG AAC TTG    62
pH3-6α                                            17                      47
                         Sal I
Cl-Δ4                    GTC GAC TCT AGG CAC CAC TGA GCC ATG GAT TGG CTG TGG AAC TTG
                                          32
              Sal I
Cl-Δ21        GT CGA CTC TAG TTT GTC TTA AGG CAC CAC TGA GCC ATG GAT TGG CTG TGG AAC TTG
                                                                    JH2  Cγ2a (MOUSE)
              Sal I                                                 ⎯⎯⎯⎯⎯⎯⎯⎯⎯⎯⎯⎯⎯⎯
              GTC GAC TCT AGG CAC CAC TGA ⟨ CAA GGC ACC ACT CTC ACA GTC TCC TCA GCC AAA ACA ACA GCC CCA TCG GTC
                                      VH          Gln Gly Thr Thr Leu Thr Val Ser Ser Ala Lys Thr Thr Ala Pro Ser Val
                                                                465                      480                      495
              Sal I                                                                              xx      xx   x
              GT CGA CTC TAG TTT GTC TTA AGG CAC CAC TGA ⟨ ──────⟩ TGT CAG AGG AGT CGG TCG TGT TTC CCG GGT A MJH-2 ApaI
                                      VH                         Ala Ser Thr Lys Gly Pro                              510
                                                                         Cγ1 (HUMAN)
```

FIG. 7A

L6 Chimerae $V_H$ pH3-6a ($J_H$2) oligo (dT) clone, BAL-31 deletions 5', $C_\gamma$'APA mutagenesis → pING 2111 neo
pING 2112 neo

```
      SalI        pING 2111       pING 2112
       ↓             ↓               ↓
5'  GTCGACTCTAG TTTGTCTTAAGG CACCACTGAGCCCAAG
              met
              TCTTAGACATCGGAT
```

```
                                           mo|hu
joint   ACCACTCTCACAGTCTCCTCA|GCCAGCACAAAGGGC
        ApaI
        ↓
        CCAT
```

$V_K$ pL3-12a ($J_K$5) oligo (dT) clone, $J_K$HindIII mutagenesis, 5'SAL mutagenesis → pING 2119 neo
pING 2120 gpt

```
     SalI        met
      ↓
5'  GTCGACAAAATGGAT
```

```
                 mo|hu       C_K
joint  ACCAAGCTGAGATGAAA|CGAACT
```

FIG. 10

CHIMERIC ANTIBODY WITH SPECIFICITY TO HUMAN TUMOR ANTIGEN

RELATED APPLICATIONS

This application is a continuation of application Ser. No. 07/614,954, filed on Nov. 15, 1990 and now abandoned, which is a continuation of application Ser. No. 06/923,944, filed on Oct. 27, 1986 and now abandoned.

BACKGROUND OF THE INVENTION

1. Field of the Invention

This invention relates to recombinant DNA methods of preparing an antibody with human tumor antigen specificity, genetic sequences coding therefor, as well as methods of obtaining such sequences.

2. Background Art

The application of cell-to-cell fusion for the production of monoclonal antibodies by Kohler and Milstein (*Nature* (London), 256:495, 1975) spawned a revolution in biology equal in impact to that from the invention of recombinant DNA cloning. Monoclonal antibodies produced from hybridomas are already widely used in clinical and basic scientific studies. Applications of human B cell hybridoma-produced monoclonal antibodies hold great promise for the treatment of cancer, viral and microbial infections, B cell immunodeficiencies with diminished antibody production, and other diseases and disorders of the immune system.

Unfortunately, a number of obstacles exist with respect to the development of human monoclonal antibodies. This is especially true when attempting to develop monoclonal antibodies which define human tumor antigens for the diagnosis and treatment of cancer. Many of these tumor antigens are not recognized as foreign antigens by the human immune system, therefore, these antigens may not be immunogenic in man. By contrast, those human tumor antigens which are immunogenic in mice can be used for the production of mouse monoclonal antibodies that specifically recognize the human antigen and which may be used therapeutically in humans. However, repeated injections of "foreign" antibodies, such as a mouse antibody, in humans, can lead to harmful hypersensitivity reactions as well as increased rate of clearance of the circulating antibody molecules so that the antibodies do not reach their target site.

Another problem faced by immunologists is that most human monoclonal antibodies obtained in cell culture are of the IgM type. When it is desirable to obtain human monoclonals of the IgG type, however, it has been necessary to use such techniques as cell sorting, to identify and isolate the few cells which are producing antibodies of the IgG or other type from the majority producing antibodies of the IgM type. A need therefore exists for an efficient method of switching antibody classes, for any given antibody of a predetermined or desired antigenic specificity.

The present invention bridges both the hybridoma and genetic engineering technologies to provide a quick and efficient method, as well as products derived therefrom, for the production of a chimeric human/non-human antibody.

The chimeric antibodies of the present invention embody a combination of the advantageous characteristics of monoclonal antibodies derived from mouse-mouse hybridomas and of human monoclonal antibodies. The chimeric monoclonal antibodies, like mouse monoclonal antibodies, can recognize and bind to a human target antigen; however, unlike mouse monoclonal antibodies, the species-specific properties of the chimeric antibodies will avoid the inducement of harmful hypersensitivity reactions and will allow for resistance to clearance when used in humans in vivo. Moreover, using the methods disclosed in the present invention, any desired antibody isotype can be conferred upon a particular antigen combining site.

INFORMATION DISCLOSURE STATEMENT*

Approaches to the problem of producing chimeric antibodies have been published by various authors.

*Note: The present Information Disclosure Statement is subject to the provisions of 37 C.F.R. 1.97(b). In addition, Applicants reserve the right to demonstrate that their invention was made prior to any one or more of the mentioned publications.

Morrison, S. L. et al., *Proc. Natl. Acad. Sci.*, U.S.A., 81:6851–6855 (November 1984), describe the production of a mouse-human antibody molecule of defined antigen binding specificity, produced by joining the variable region genes of a mouse antibody-producing myeloma cell line with known antigen binding specificity to human immunoglobulin constant region genes using recombinant DNA techniques. Chimeric genes were constructed, wherein the heavy chain variable region exon from the myeloma cell line S107 were joined to human IgG1 or IgG2 heavy chain constant region exons, and the light chain variable region exon from the same myeloma to the human kappa light chain exon. These genes were transfected into mouse myeloma cell lines and. Transformed cells producing chimeric mouse-human antiphosphocholine antibodies were thus developed.

Morrison, S. L. et al., European Patent Publication No. 173494 (published Mar. 5, 1986), disclose chimeric "receptors" (e.g. antibodies) having variable regions derived from one species and constant regions derived from another. Mention is made of utilizing cDNA cloning to construct the genes, although no details of cDNA cloning or priming are shown. (see pp 5, 7 and 8).

Boulianne, G. L. et al., *Nature*, 312: 643 (Dec. 13, 1984), also produced antibodies consisting of mouse variable regions joined to human constant regions. They constructed immunoglobulin genes in which the DNA segments encoding mouse variable regions specific for the hapten trinitrophenyl (TNP) were joined to segments encoding human mu and kappa constant regions. These chimeric genes were expressed as functional TNP binding chimeric IgM.

For a commentary on the work of Boulianne et al. and Morrison et al., see Munro, *Nature*, 312:597 (Dec. 13, 1984), Dickson, *Genetic Engineering News*, 5, No. 3 (March 1985), or Marx, *Science*, 229:455 (August 1985).

Neuberger, M. S. et al., *Nature*, 314:268 (Mar. 25, 1985), also constructed a chimeric heavy chain immunoglobulin gene in which a DNA segment encoding a mouse variable region specific for the hapten 4-hydroxy-3-nitrophenacetyl (NP) was joined to a segment encoding the human epsilon region. When this chimeric gene was transfected into the J558L cell line, an antibody was produced which bound to the NP hapten and had human IgE properties.

Neuberger, M. S. et al., have also published work showing the preparation of cell lines that secrete hapten-specific antibodies in which the Fc portion has been replaced either with an active enzyme moiety (Williams, G. and Neuberger, M. S. *Gene* 43:319, 1986) or with a polypeptide displaying c-myc antigenic determinants (*Nature*, 312:604, 1984).

Neuberger, M. et al., PCT Publication WO 86/01533, (published Mar. 13, 1986) also disclose production of chimeric antibodies (see p. 5) and suggests, among the technique's many uses the concept of "class switching" (see p. 6).

Taniguchi, M., in European Patent Publication No. 171 496 (published Feb. 19, 1985) discloses the production of chimeric antibodies having variable regions with tumor specificity derived from experimental animals, and constant regions derived from human. The corresponding heavy and light chain genes are produced in the genomic form, and expressed in mammalian cells.

Takeda, S. et al., *Nature*, 314:452 (Apr. 4, 1985) have described a potential method for the construction of chimeric immunoglobulin genes which have intron sequences removed by the use of a retrovirus vector. However, an unexpected splice donor site caused the deletion of the V region leader sequence. Thus, this approach did not yield complete chimeric antibody molecules.

Cabilly, S. et al., *Proc. Natl. Acad. Sci. U.S.A.*, 81:3273-3277 (June 1984), describe plasmids that direct the synthesis in *E. coli* of heavy chains and/or light chains of anti-carcinoembryonic antigen (CEA) antibody. Another plasmid was constructed for expression of a truncated form of heavy chain (Fd) fragment in *E. coli*. Functional CEA-binding activity was obtained by in vitro reconstitution, in *E. coli* extracts, of a portion of the heavy chain with light chain.

Cabilly, S., et al., European Patent Publication 125023 (published Nov. 14, 1984) describes chimeric immunoglobulin genes and their presumptive products as well as other modified forms. On pages 21, 28 and 33 it discusses cDNA cloning and priming.

Boss, M. A., European Patent Application 120694 (published Oct. 3, 1984) shows expression in *E. coli* of non-chimeric immunoglobulin chains with 4-nitrophenyl specificity. There is a broad description of chimeric antibodies but no details (see p. 9).

Wood, C. R. et al., *Nature*, 314: 446 (April, 1985) describe plasmids that direct the synthesis of mouse anti-NP antibody proteins in yeast. Heavy chain mu antibody proteins appeared to be glycosylated in the yeast cells. When both heavy and light chains were synthesized in the same cell, some of the protein was assembled into functional antibody molecules, as detected by anti-NP binding activity in soluble protein prepared from yeast cells.

Alexander, A. et al., *Proc. Nat. Acad. Sci. U.S.A.*, 79:3260-3264 (1982), describe the preparation of a cDNA sequence coding for an abnormally short human Ig gamma heavy chain (OMM gamma$^3$ HCD serum protein) containing a 19- amino acid leader followed by the first 15 residues of the V region. An extensive internal deletion removes the remainder of the V and the entire $C_H1$ domain. This is cDNA coding for an internally deleted molecule.

Dolby, T. W. et al., *Proc. Natl. Acad. Sci. U.S.A.*, 77:6027-6031 (1980), describe the preparation of a cDNA sequence and recombinant plasmids containing the same coding for mu and kappa human immunoglobulin polypeptides. One of the recombinant DNA molecules contained codons for part of the $CH_3$ constant region domain and the entire 3noncoding sequence.

Seno, M. et al., *Nucleic Acids Research*, 11:719-726 (1983), describe the preparation of a cDNA sequence and recombinant plasmids containing the same coding for part of the variable region and all of the constant region of the human IgE heavy chain (epsilon chain).

Kurokawa, T. et al., ibid, 11: 3077-3085 (1983), show the construction, using cDNA, of three expression plasmids coding for the constant portion of the human IgE heavy chain.

Liu, F. T. et al., *Proc. Nat. Acad. Sci., U.S.A.*, 81:5369-5373 (September 1984), describe the preparation of a cDNA sequence and recombinant plasmids containing the same encoding about two-thirds of the $CH_2$, and all of the $C_H3$ and $C_H4$ domains of human IgE heavy chain.

Tsujimoto, Y. et al., *Nucleic Acids Res.*, 2:8407-8414 (November 1984), describe the preparation of a human V lambda cDNA sequence from an Ig lambda-producing human Burkitt lymphoma cell line, by taking advantage of a cloned constant region gene as a primer for cDNA synthesis.

Murphy, J., PCT Publication WO 83/03971 (published Nov. 24, 1983) discloses hybrid proteins made of fragments comprising a toxin and a cell-specific ligand (which is suggested as possibly being an antibody).

Tan, et al., *J. Immunol.* 135:8564 (November, 1985), obtained expression of a chimeric human-mouse immunoglobulin genomic gene after transfection into mouse myeloma cells.

Jones, P. T., et al., *Nature* 321:552 (May 1986) constructed and expressed a genomic construct where CDR domains of variable regions from a mouse monoclonal antibody were used to substitute for the corresponding domains in a human antibody.

Sun, L. K., et al., *Hybridoma* 5 suppl. 1 S17 (1986), describes a chimeric human/mouse antibody with potential tumor specificity. The chimeric heavy and light chain genes are genomic constructs and expressed in mammalian cells.

Sahagan et al., *J. Immun.* 137:1066-1074 (August 1986) describe a chimeric antibody with specificity to a human tumor associated antigen, the genes for which are assembled from genomic sequences.

For a recent review of the field see also Morrison, S. L., *Science* 229: 1202-1207 (Sep. 20, 1985) and Oi, V. T., et al., *BioTechniques* 4:214 (1986).

The Oi, et al., paper is relevant as it argues that the production of chimeric antibodies from cDNA constructs in yeast and/or bacteria is not necessarily advantageous.

See also Commentary on page 835 in *Biotechnology* 4 (1986).

SUMMARY OF THE INVENTION

The invention provides a genetically engineered chimeric antibody of desired variable region specificity and constant region properties, through gene cloning and expression of light and heavy chains. The cloned immunoglobulin gene products can be produced by expression in genetically engineered cells.

The application of oligodeoxynucleotide synthesis, recombinant DNA cloning, and production of specific immunoglobulin chains in various procaryotic and eucaryotic cells provides a means for the large scale production of a chimeric human/mouse monoclonal antibody with specificity to a human tumor antigen.

The invention provides cDNA sequences coding for immunoglobulin chains comprising a constant human region and a variable, non-human, region. The immunoglobulin chains can either be heavy or light.

The invention provides gene sequences coding for immunoglobulin chains comprising a cDNA variable region of the desired specificity. These can be combined with genomic constant regions of human origin.

The invention provides sequences as above, present in recombinant DNA molecules in vehicles such as plasmid vectors, capable of expression in desired prokaryotic or eukaryotic hosts.

The invention provides hosts capable of producing, by culture, the chimeric antibodies and methods of using these hosts.

The invention also provides individual chimeric immunoglobulin individual chains, as well as complete assembled molecules having human constant regions and variable regions with a human tumor antigen specificity, wherein both variable regions have the same binding specificity.

Among other immunoglobulin chains and/or molecules provided by the invention are:

(a) a complete functional, immunoglobulin molecule comprising:
(i) two identical chimeric heavy chains comprising a variable region with a human tumor antigen specificity and human constant region and
(ii) two identical all (i.e. non-chimeric) human light chains.

(b) a complete, functional, immunoglobulin molecule comprising:
(i) two identical chimeric heavy chains comprising a variable region as indicated, and a human constant region, and
(ii) two identical all (i.e. non-chimeric) non-human light chains.

(c) a monovalent antibody, i.e., a complete, functional immunoglobulin molecule comprising:
(i) two identical chimeric heavy chains comprising a variable region as indicated, and a human constant region, and
(ii) two different light chains, only one of which has the same specificity as the variable region of the heavy chains. The resulting antibody molecule binds only to one end thereof and is therefore incapable of divalent binding.

Genetic sequences, especially cDNA sequences, coding for the aforementioned combinations of chimeric chains or of non-chimeric chains are also provided herein.

The invention also provides for a genetic sequence, especially a cDNA sequence, coding for the variable region of desired specificity of an antibody molecule heavy and/or light chain, operably linked to a sequence coding for a polypeptide different than an immunoglobulin chain (e.g., an enzyme). These sequences can be assembled by the methods of the invention, and expressed to yield mixed-function molecules.

The use of cDNA sequences is particularly advantageous over genomic sequences (which contain introns), in that cDNA sequences can be expressed in bacteria or other hosts which lack appropriate RNA splicing systems.

BRIEF DESCRIPTION OF THE FIGURES

FIGS. 2A and 2B above shows the known nucleotide sequences of human and mouse J regions. Consensus sequences for the J regions are shown below the actual sequences. The oligonucleotide sequence below the mouse kappa J region consensus sequence is a Universal Immunoglobulin Gene (UIG) oligonucleotide. Note that there are only a few J regions with relatively conserved sequences, especially near the constant regions, in each immunoglobulin gene locus.

FIG. 3 shows the nucleotide sequences of the mouse J regions. Shown below are the oligonucleotide primers UIG-H and UIG-K. Note that each contains a restriction enzyme site. They can be used as primers for the synthesis of cDNA complementary to the variable region of mRNA, and can also be used to mutagenize, in vitro, cloned cDNA.

FIG. 4 Human Constant Domain Module.

The human C gamma 1 clone, pGMH6, was isolated from the cell line GM2146. The sequence at its $J_H$-$C_H1$ junction is shown. Two restriction enzyme sites are useful as joints in recombining the $C_H1$ gene with different $V_H$ genes. The BstEII site is in the $J_H$ region, and was used in a previous construction of a mouse-human chimeric heavy-chain immunoglobulin. The ApaI site is 16 nucleotide residues into the $C_H1$ coding domain of Human gamma 1; and is used in the construction described in this application.

The human $C_K$ clone, pGML60, is a composite of two cDNA clones, one isolated from GM1500 (pK2-3), the other from GM2146 (pGML1). The $J_K$-$C_K$ junction sequence shown comes from pK2-3. In vitro mutagenesis using the oligonucleotide, JKHindIII, was carried out to engineer a HindIII site 14 nucleotide residues 5' of the J-C junction. This changes a human GTG codon into a CTT codon.

Figure 5A:
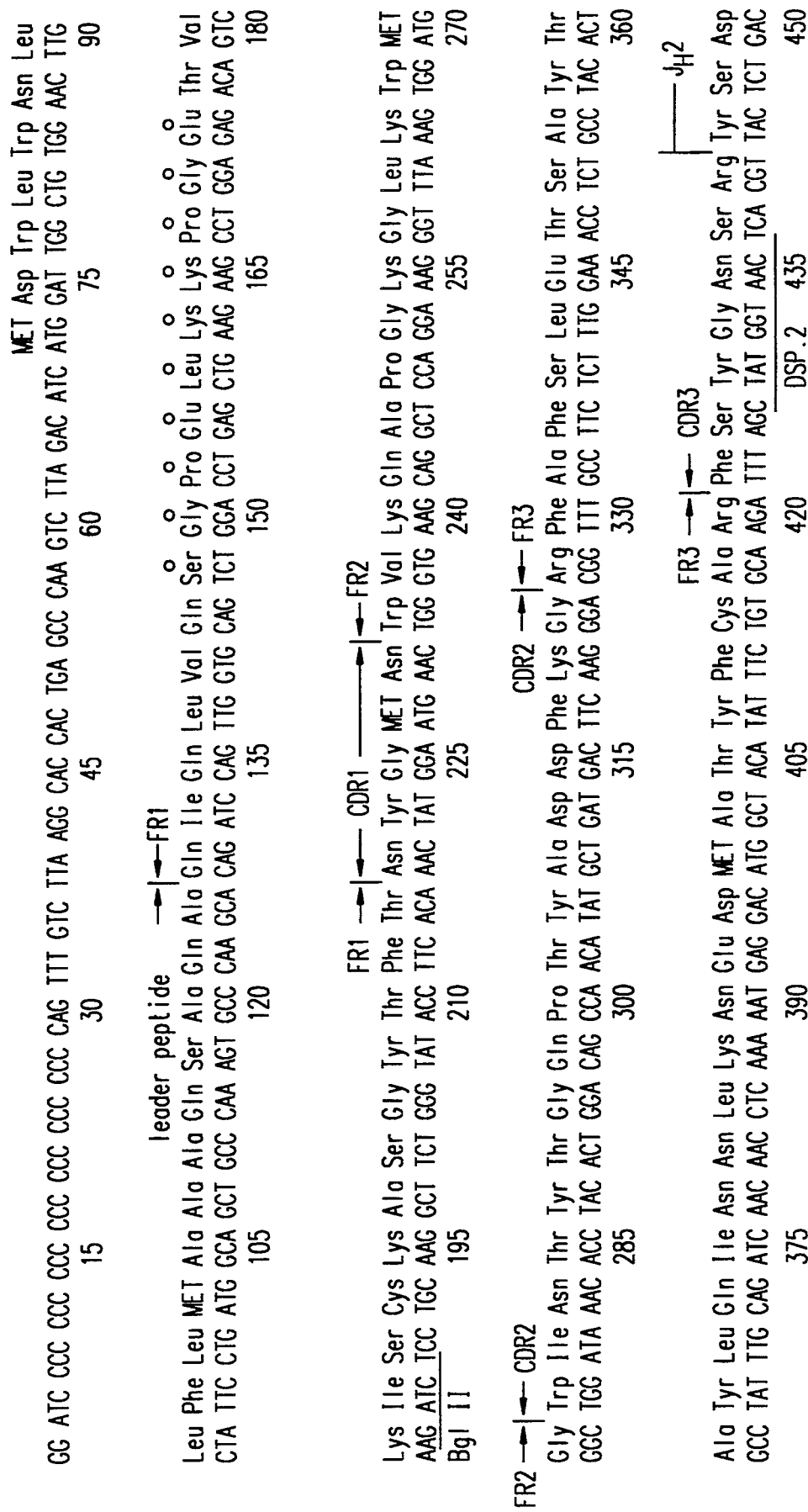
Figure 5B:
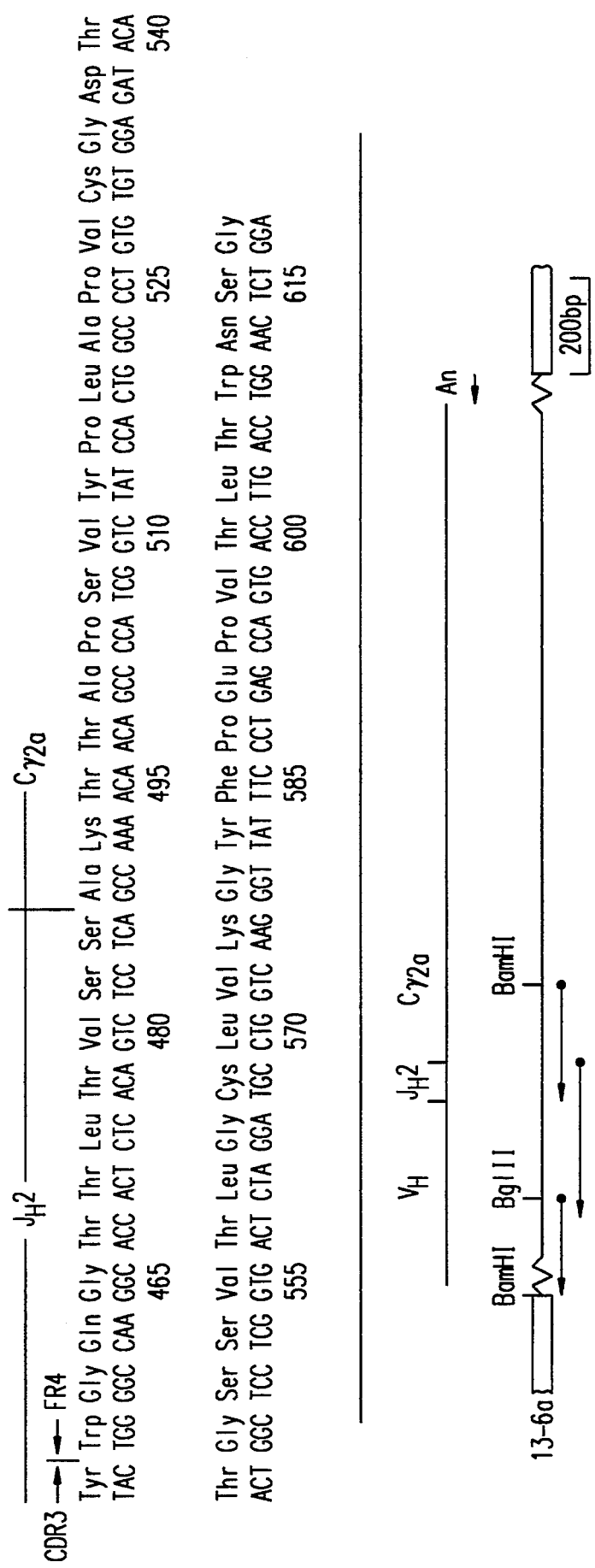

FIGS. 5A and 5B shows the nucleotide sequence of the V region of the L6 $V_H$ cDNA clone pH3-6a. The sequence was determined by the dideoxytermination method using M13 subclones of gene fragments (shown below). Open circles denote amino acid residues confirmed by peptide sequence. A sequence homologous to $D_{SP2}$ in the CDR3 region is underlined.

Figure 6:
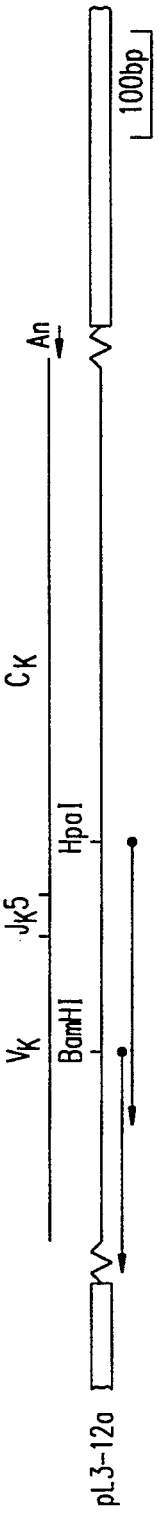

FIG. 6 shows the nucleotide sequence of the V region of the L6 $V_K$ cDNA clone pL3-12a. The oligonucleotide primer used for site-directed mutagenesis is shown below the $J_K5$ segment. Open circles denote amino acid residues confirmed by peptide sequence.

Figure 7B:
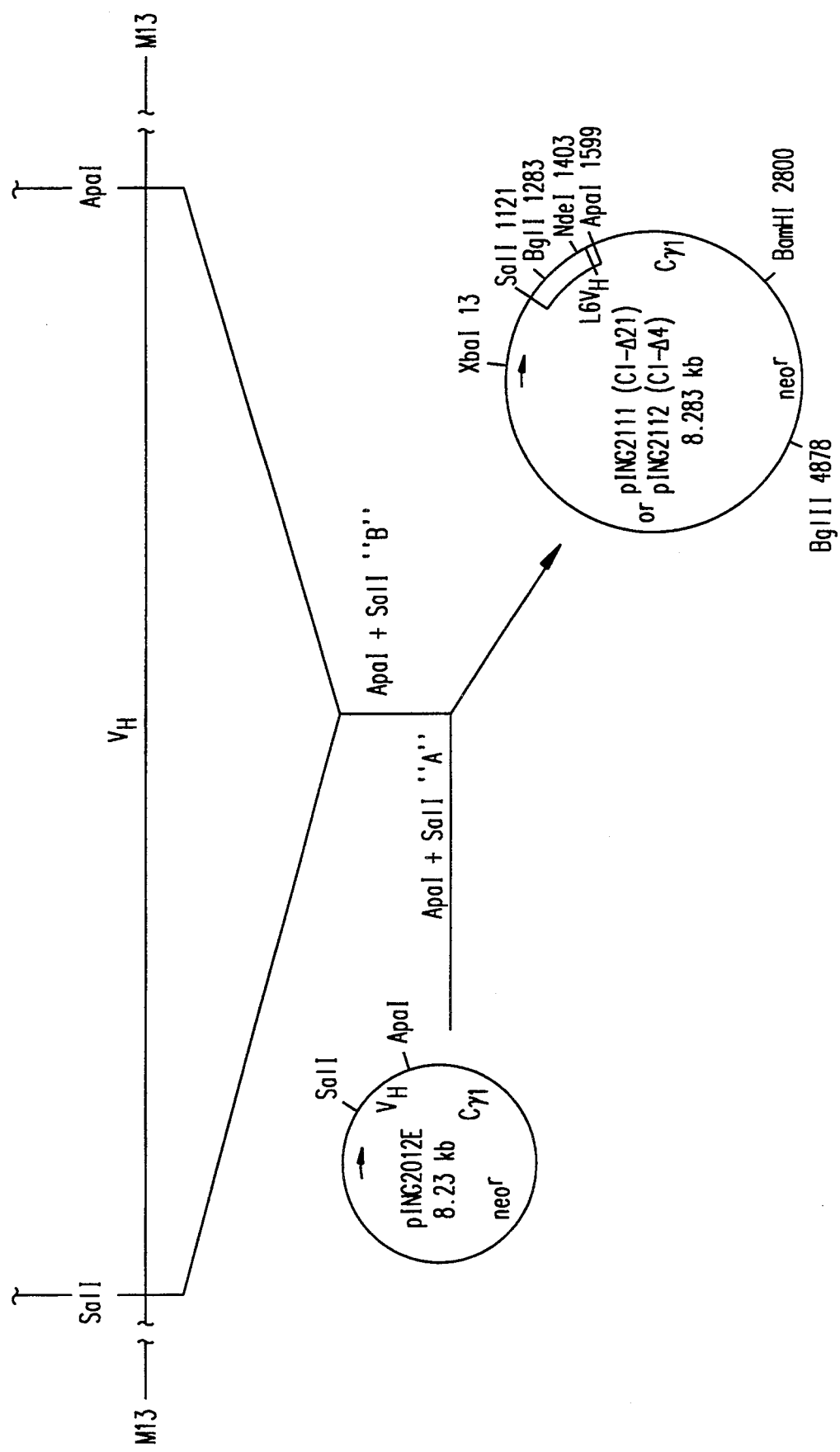

FIGS. 7A and 7B shows the construction of chimeric L6-$V_H$ plus human C gamma 1 expression plasmids. FIG. 7A shows the sequences of the BAL-31 deletion clones M13mp19-Cl-delta 4 (Cl-delta 4) and M13mp19-Cl-delta 21(Cl- delta 21). The 5' end of the cDNA clone, pH3-6a, is denoted with an arrow. M13 sequences are underlined. The oligonucleotide primer used for this experiment is H3-6a (5'-GACTGCACCAACTGG-3'), which primes in FR1 near the mature N terminus. FIG. 7A also shows the strategy for site-directed mutagenesis of 1 ug of clones Cl-delta 4 and Cl-delta 21, each annealed to 20 ng of the 31-mer oligonucleotide MJ$_H$2-ApaI. Complementary strand synthesis with the Klenow fragment of DNA polymerase was at room temperature for 30 min, then 15° C. for 72 hours. Transfected phage plaques were adsorbed to nitrocellulose, fixed with NaOH, and hybridized to $^{32}$P-labelled MJH2-ApaI oligonucleotide at 65° C. 18 hours, in 4×TBS (0.6M NaCl, 0.04 M Tris-HCl (pH 7.4), 0.004M EDTA) plus 10% dextran sulfate. Final wash of the filters was at 65° C. 4×SSPE, 0.1% SDS for 15 min. (Maniatis, T., et al., *Molecular Cloning: A Laboratory Manual,* 1982). Positive plaques were detected by overnight exposure to Kodak XAR film, and were directly picked for growth and restriction enzyme analysis of RF DNA. Mismatches of the MJH2-ApaI oligonucleotide to the mouse $C_H1$ are denoted, resulting in the coding changes shown below the oligonucleotide. Panel (c) shows the strategy of the substitution of each of the mutagenized L6-$V_H$ modules for the resident $V_H$ of the chimeric expression plasmid pING2012 to generate pING2111 and pING2112.

Figure 8:
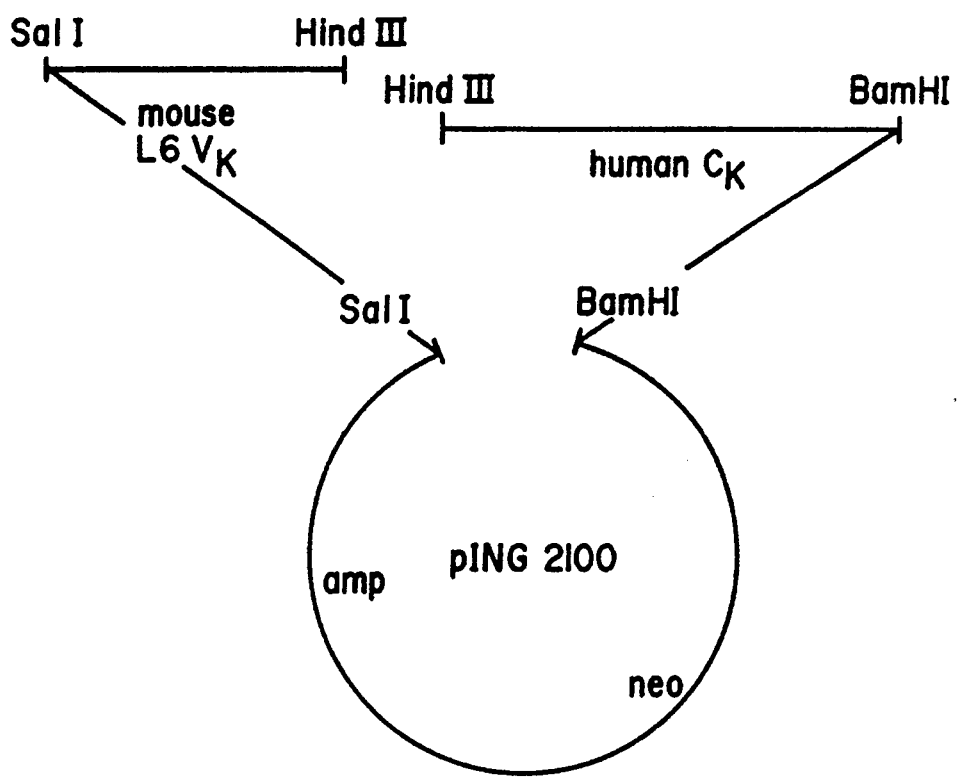

FIG. 8 shows the construction of the chimeric L6 expression plasmid pING2119. The SalI to BamHI fragment from pING2100 is identical to the SalI to BamHI A fragment from pING2012E.

Figure 9A:
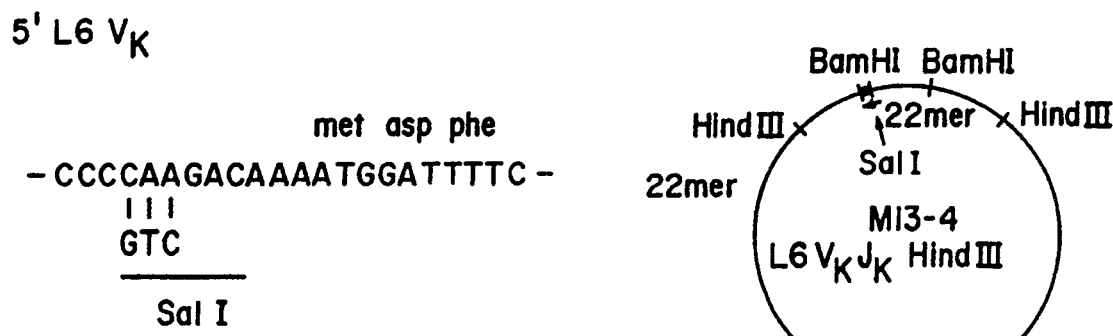
Figure 9B:
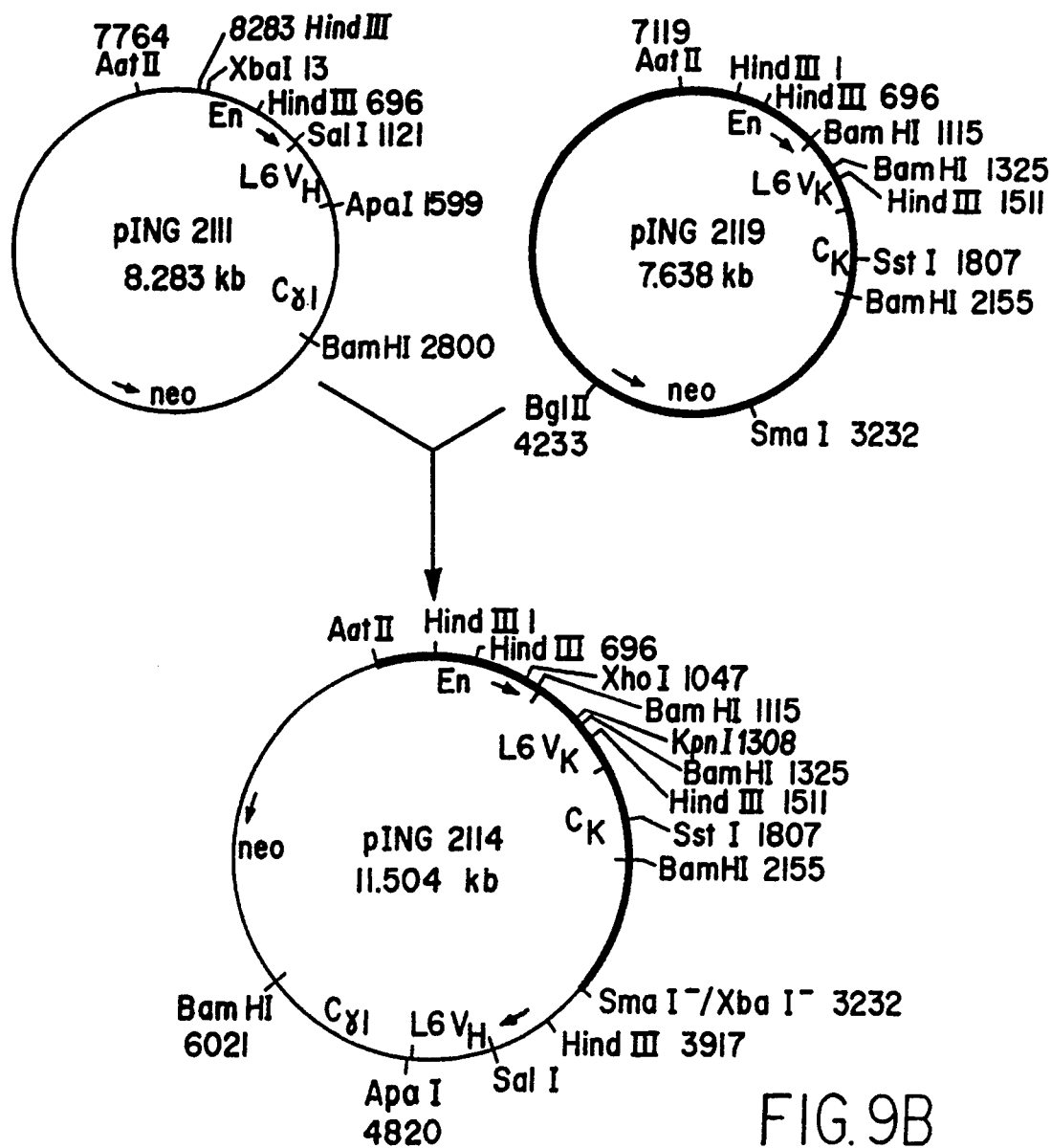

FIGS. 9A and 9B shows the modification of the $V_K$ gene and its use in constructing light chain and heavy plus light chain expression plasmids.

Deletion of the oligo d[GC] segment 5' of $V_K$ of L6. The oligonucleotide is a 22-mer and contains a SalI site. The 3 mismatches are shown. The $V_K$ gene, after mutagenesis, is joined as a SalI-HindIII fragment to the human C K module. The expression plasmid thus formed is pING2119.

FIG. 9B pING2114, a heavy plus light chain expression plasmid. The expression plasmid pING2114 contains the L6 heavy chain chimeric gene from pING2111 and the chimeric light chain from pING2119 (bold line).

FIG. 10 shows a summary of the sequence alterations made in the construction of the L6 chimeric antibody expression plasmids. Residues underlined in the 5' untranslated region are derived from the cloned mouse kappa and heavy- chain genes. Residues circled in the V/C boundary result from mutagenesis operations to engineer restriction enzyme sites in this region. Residues denoted by small circles above them in the L6 heavy-chain chimera also result from mutagenesis. They are silent changes.

DESCRIPTION OF THE PREFERRED EMBODIMENTS

INTRODUCTION

Generally, antibodies are composed of two light and two heavy chain molecules. Light and heavy chains are divided into domains of structural and functional homology. The variable domains of both the light ($V_L$) and the heavy ($V_H$) chains determine recognition and specificity. The constant region domains of light ($C_L$) and heavy ($C_H$) chains confer important biological properties such as antibody chain association, secretion, transplacental mobility, complement binding, and the like.

Figure 1:
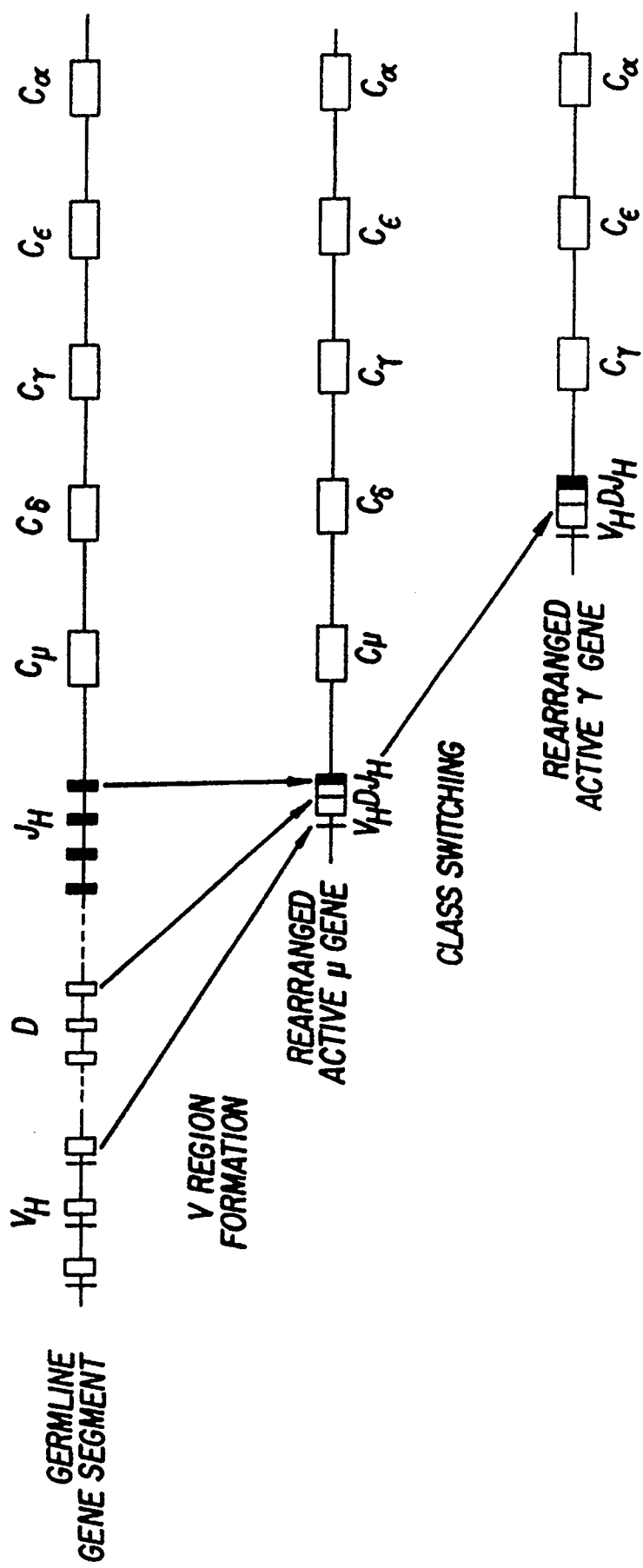
FIG. 1 shows the DNA rearrangements and the expression of immunoglobulin mu and gamma heavy chain genes. This is a schematic representation of the human heavy chain gene complex, not shown to scale. Heavy chain variable V region formation occurs through the proper joining of $V_H$, D and $J_H$ gene segments. This generates an active mu gene. A different kind of DNA rearrangement called "class switching" relocates the joined $V_H$, D and $J_H$ region from the vicinity of mu constant C region to that of another heavy chain C region (switching to gamma is diagrammed here).

A complex series of events leads to immunoglobulin gene expression in B cells. The V region gene sequences conferring antigen specificity and binding are located in separate germ line gene segments called $V_H$, D and $J_H$; or $V_L$ and $J_L$. These gene segments are joined by DNA rearrangements to form the complete V regions expressed in heavy and light chains respectively (FIG. 1). The rearranged, joined ($V_L$—$J_L$ and $V_H$—D—$J_H$) V segments then encode the complete variable regions or antigen binding domains of light and heavy chains, respectively.

DEFINITIONS

Certain terms and phrases are used throughout the specification and claims. The following definitions are provided for purposes of clarity and consistency.

1. Expression vector—a plasmid DNA containing necessary regulatory signals for the synthesis of mRNA derived from any gene sequence, inserted into the vector.

2. Module vector—a plasmid DNA containing a constant or variable region gene module.

3. Expression plasmid—an expression vector that contains an inserted gene, such as a chimeric immunoglobulin gene.

4. Gene cloning—synthesis of a gene, insertion into DNA vectors, identification by hybridization, sequence analysis and the like.

5. Transfection—the transfer of DNA into mammalian cells.

GENETIC PROCESSES AND PRODUCTS

The invention provides a novel approach for the cloning and production of a human/mouse chimeric antibody with specificity to a human tumor antigen. The antigen is that bound by the monoclonal antibody described in *Cancer Res.* 46:3917–3923 (1986), and in *Proc. Nat. Acad. Sci.* U.S.A. 83:7059–7063 (1986). The hybridoma secreting this monoclonal antibody was deposited at the American Type Culture Collection, Rockville, Maryland on Dec. 6, 1984 with accession No. NB 8677.

The method of production combines five elements:

(1) Isolation of messenger RNA (mRNA) from the mouse B cell hybridoma line producing the monoclonal antibody, cloning and cDNA production therefrom;

(2) Preparation of Universal Immunoglobulin Gene (UIG) oligonucleotides, useful as primers and/or probes for cloning of the variable region gene segments in the light and heavy chain mRNA from the hybridoma cell line, and cDNA production therefrom;

(3) Preparation of constant region gene segment modules by cDNA preparation and cloning, or genomic gene preparation and cloning;

(4) Construction of complete heavy or light chain coding sequences by linkage of the cloned specific immunoglobulin variable region gene segments of part (2) above to cloned human constant region gene segment modules;

(5) Expression and production of light and heavy chains in selected hosts, including prokaryotic and eukaryotic cells, either in separate fermentations followed by assembly of antibody molecules in vitro., or through production of both chains in the same cell.

One common feature of all immunoglobulin light and heavy chain genes and the encoded messenger RNAs is the so-called J region (i.e. joining region, see FIG. 1). Heavy and light chain J regions have different sequences, but a high degree of sequence homology exists (greater than 80%) especially near the constant region, within the heavy $J_H$ regions or the kappa light chain J regions. This homology is exploited in this invention and consensus sequences of light and heavy chain J regions were used to design oligonucleotides (designated herein as UIGs) for use as primers or probes for cloning immunoglobulin light or heavy chain mRNAs or genes (FIG. 3). Depending on the sequence of a particular UIG, it may be capable of hybridizing to all immunoglobulin mRNAs or genes containing a single specific J sequence. Another utility of a particular UIG probe may be hybridization to light chain or heavy chain mRNAs of a specific constant region, such as UIG-MJK which detects all mouse $J_K$ containing sequences (FIGS. 2A and 2B). UIG design can also include a sequence to introduce a restriction enzyme site into the cDNA copy of an immunoglobulin gene (see FIG. 3). The invention may, for example, utilize chemical gene synthesis to generate the UIG probes for the cloning and modification of V regions in immunoglobulin mRNA. On the other hand, oligonucleotides can be synthesized to recognize individually, the less conserved 5'-region of the J regions as a diagnostic aid in identifying the particular J region present in the immunoglobulin mRNA.

On the other hand oligonucleotides can be synthesized to recognize individually the less conserved 5' region of the J region as a diagnostic aid in identifying the particular J region present in the Ig mRNA.

A multi-step procedure is utilized for generating complete V+C region cDNA clones from the hybridoma cell light and heavy chain mRNAs. First, the complementary strand of oligo (dT)-primed cDNA is synthesized, and this double-stranded cDNA is cloned in appropriate cDNA cloning vectors such as pBR322 (Gubler and Hoffman, Gene, 25: 263 (1983)). Clones are screened by hybridization with UIG oligonucleotide probes. Positive heavy and light chain clones identified by this screening procedure are mapped and sequenced to select those containing V region and leader coding sequences. In vitro mutagenesis including, for example, the use of UIG oligonucleotides, is then used to engineer desired restriction enzyme cleavage sites.

An alternative method is to use synthetic UIG oligonucleotides as primers for the synthesis of cDNA.

Second, cDNA constant region module vectors are prepared from human cells. These cDNA clones are modified, when necessary, by site-directed mutagenesis to place a restriction site at the analogous position in the human sequence or at another desired location near a boundary of the constant region. An alternative method utilizes genomic C region clones as the source for C region module vectors.

Third, cloned V region segments generated as above are excised and ligated to light or heavy chain C region module vectors. For example, one can clone the complete human kappa light chain C region and the complete human gamma$_1$ C region. In addition, one can modify the human gamma$_1$ region to introduce a termination codon and thereby obtain a gene sequence which encodes the heavy chain portion of an Fab molecule.

The coding sequences having operationally linked V and C regions are then transferred into appropriate expression vehicles for expression in appropriate hosts, prokaryotic or eukaryotic. Operationally linked means in-frame joining of coding sequences to derive a continuously translatable gene sequence without alterations or interruptions of the triplet reading frame.

One particular advantage of using cDNA genetic sequences in the present invention is the fact that they code continuously for immunoglobulin chains, either heavy or light. By "continuously" is meant that the sequences do not contain introns (i.e. are not genomic sequences, but rather, since derived from mRNA by reverse transcription, are sequences of contiguous exons). This characteristic of the cDNA sequences provided by the invention allows them to be expressible in prokaryotic hosts, such as bacteria, or in lower eukaryotic hosts, such as yeast.

Another advantage of using cDNA cloning method is the ease and simplicity of obtaining variable region gene modules.

The terms "constant" and "variable" are used functionally to denote those regions of the immunoglobulin chain, either heavy or light chain, which code for properties and features possessed by the variable and constant regions in natural non-chimeric antibodies. As noted, it is not necessary for the complete coding region for variable or constant regions to be present, as long as a functionally operating region is present and available.

Expression vehicles include plasmids or other vectors. Preferred among these are vehicles carrying a functionally complete human constant heavy or light chain sequence having appropriate restriction sites engineered so that any variable heavy or light chain sequence with appropriate cohesive ends can be easily inserted thereinto. Human constant heavy or light chain sequence-containing vehicles are thus an important embodiment of the invention. These vehicles can be used as intermediates for the expression of any desired complete heavy or light chain in any appropriate host.

One preferred host is yeast. Yeast provides substantial advantages for the production of immunoglobulin light and heavy chains. Yeasts carry out post-translational peptide modifications including glycosylation. A number of recombinant DNA strategies now exist which utilize strong promoter sequences and high copy number plasmids which can be used for overt production of the desired proteins in yeast. Yeast recognizes leader sequences on cloned mammalian gene products and secretes peptides bearing leader sequences (i.e. prepeptides) (Hitzman, et al., 11th International Conference on Yeast, Genetics and Molecular Biology, Montpelier, France, Sep. 13–17, 1982).

Yeast gene expression systems can be routinely evaluated for the level of heavy and light chain production, protein stability, and secretion. Any of a series of yeast gene expression systems incorporating promoter and termination elements from the actively expressed genes coding for glycolytic enzymes produced in large quantities when yeasts are grown in mediums rich in glucose can be utilized. Known glycolytic genes can also provide very efficient transcription control signals. For example, the promoter and terminator signals of the iso-1-cytochrome C (CYC-1) gene can be utilized.

The following approach can be taken for evaluating optimal expression plasmids for the expression of cloned immunoglobulin cDNAs in yeast.

(1) The cloned immunoglobulin DNA linking V and C regions is attached to different transcription promoters and terminator DNA fragments;

(2) The chimeric genes are placed on yeast plasmids (see, for example, Broach, J. R. in Methods in Enzymology—Vol. 101:307 ed. Wu, R. et al., 1983));

(3) Additional genetic units such as a yeast leader peptide may be included on immunoglobulin DNA constructs to obtain antibody secretion.

(4) A portion of the sequence, frequently the first 6 to 20 codons of the gene sequence may be modified to represent preferred yeast codon usage.

(5) The chimeric genes are placed on plasmids used for integration into yeast chromosomes.

The following approaches can be taken to simultaneously express both light and heavy chain genes in yeast.

(1) The light and heavy chain genes are each attached to a yeast promoter and a terminator sequence and placed on the same plasmid. This plasmid can be designed for either autonomous replication in yeast or integration at specific sites in the yeast chromosome.

(2) The light and heavy chain genes are each attached to a yeast promoter and terminator sequence on separate plasmids containing different selective markers. For example, the light chain gene can be placed on a plasmid containing the trp1 gene as a selective marker, while the heavy chain gene can be placed on a plasmid containing ura3 as a selective marker. The plasmids can be designed for either autonomous replication in yeast or integration at specific sites in yeast chromosomes. A yeast strain defective for both selective markers is either simultaneously or sequentially transformed with the plasmid containing the light chain gene and with the plasmid containing the heavy chain gene.

(3) The light and heavy chain genes are each attached to a yeast promoter and terminator sequence on separate plasmids each containing different selective markers as described in (2) above. A yeast mating type "a" strain defective in the selective markers found on the light and heavy chain expression plasmids (trp1 and ura3 in the above example) is transformed with the plasmid containing the light chain gene by selection for one of the two selective markers (trp1 in the above example). A yeast mating type "alpha" strain defective in the same selective markers as the "a" strain (i.e. trp1 and ura3 as examples) is transformed with a plasmid containing the heavy chain gene by selection for the alternate selective marker (i.e. ura3 in the above example). The "a" strain containing the light chain plasmid (phenotype: Trp+ Ura− in the above example) and the strain containing the heavy chain plasmid (pheno-type: Trp− Ura+ in the above example) are mated and diploids are selected which are prototrophic for both of the above selective markers (Trp+ Ura+ in the above example).

Among bacterial hosts which may be utilized as transformation hosts, *E. coli* K12 strain 294 (ATCC 31446) is particularly useful. Other microbial strains which may be used include *E. coli* X1776 (ATCC 31537). The aforementioned strains, as well as coli W3110 (ATCC 27325) and other enterobacteria such as *Salmonella typhimurium* or *Serratia marcescens*, and various Pseudomonas species may be used.

In general, plasmid vectors containing replicon and control sequences which are derived from species compatible with a host cell are used in connection with these hosts. The vector ordinarily carries a replication site, as well as specific genes which are capable of providing phenotypic selection in transformed cells. For example, *E. coli* is readily transformed using pBR322, a plasmid derived from an *E. coli* species (Bolivar, et al., *Gene*, 2:95 (1977)). pBR322 contains genes for ampicillin and tetracycline resistance, and thus provides easy means for identifying transformed cells. The pBR322 plasmid or other microbial plasmids must also contain, or be modified to contain, promoters which can be used by the microbial organism for expression of its own proteins. Those promoters most commonly used in recombinant DNA construction include the beta-lactamase (penicillinase) and lactose (beta-galactosidase) promoter systems (Chang et al., *Nature*, 275:615 (1978); Itakura et al., *Science*, 198:1056 (1977)); and tryptophan promoter systems (Goeddel et al., *Nucleic Acids Research*, 8:4057 (1980); EPO Publication No. 0036776). While these are the most commonly used, other microbial promoters have been discovered and utilized.

For example, a genetic construct for any heavy or light chimeric immunoglobulin chain can be placed under the control of the leftward promoter of bacteriophage lambda ($P_L$). This promoter is one of the strongest known promoters which can be controlled. Control is exerted by the lambda repressor, and adjacent restriction sites are known.

The expression of the immunoglobulin chain sequence can also be placed under control of other regulatory sequences which may be "homologous" to the organism in its untransformed state. For example, lactose dependent *E. coli* chromosomal DNA comprises a lactose or lac operon which mediates lactose digestion by elaborating the enzyme beta-galactosidase. The lac control elements may be obtained from bacteriophage lambda pLAC5, which is infective for *E. coli*. The lac promoter-operator system can be induced by IPTG.

Other promoter/operator systems or portions thereof can be employed as well. For example, arabinose, colicine E1, galactose, alkaline phosphatase, tryptophan, xylose, tac, and the like can be used.

Other preferred hosts are mammalian cells, grown in vitro in tissue culture, or in vivo in animals. Mammalian cells provide post-translational modifications to immunoglobulin protein molecules including leader peptide removal, correct folding and assembly of heavy and light chains, proper glycosylation at correct sites, and secretion of functional antibody protein.

Mammalian cells which may be useful as hosts for the production of antibody proteins include cells of lymphoid origin, such as the hybridoma Sp2/0-Ag14 (ATCC CRL 1581) or the myeloma P3X63Ag8 (ATCC TIB 9), and its derivatives. Others include cells of fibroblast origin, such as Vero (ATCC CRL 81) or CHO-K1 (ATCC CRL 61).

Several possible vector systems are available for the expression of cloned heavy chain and light chain genes in mammalian cells. One class of vectors relies upon the integration of the desired gene sequences into the host cell genome. Cells which have stably integrated DNA can be selected by simultaneously introducing drug resistance genes such as *E. coli* gpt (Mulligan, R. C. and Berg, P., *Proc. Natl. Acad. Sci.*, U.S.A., 78: 2072 (1981)) or Tn5 neo (Southern, P. J. and Berg, P., *J. Mol. Appl. Genet.*, 1:327 (1982)). The selectable marker gene can be either linked to the DNA gene sequences to be expressed, or introduced into the same cell by co-transfection (Wigler, M. et al., *Cell*, 16: 77 (1979)). A second class of vectors utilizes DNA elements which confer autonomously replicating capabilities to an extrachromosomal plasmid. These vectors can be derived from animal viruses, such as bovine papillomavirus (Sarver, N. et al., *Proc. Natl. Acad. Sci. U.S.A.*, 79:7147 (1982)), polyoma virus (Deans, R. J. et al., *Proc. Natl. Acad. Sci. U.S.A.*, 81:1292 (1984)), or SV40 virus (Lusky, M. and Botchan, M., *Nature*, 293: 79 (1981)).

Since an immunoglobulin cDNA is comprised only of sequences representing the mature mRNA encoding an antibody protein, additional gene expression elements regulating transcription of the gene and processing of the RNA are required for the synthesis of immunoglobulin mRNA. These elements may include splice signals, transcription promoters, including inducible promoters enhancers, and termination signals. cDNA expression vectors incorporating such elements include those described by Okayama, H. and Berg, P., *Mol. Cell Biol.*, 3:280 (1983); Cepko, C. L. et al., *Cell*, 37:1053 (1984); and Kaufman, R. J., *Proc. Natl. Acad. Sci., U.S.A.*, 82:689 (1985).

An additional advantage of mammalian cells as hosts is their ability to express chimeric immunoglobulin genes which are derived from genomic sequences. Thus, mammalian cells may express chimeric immunoglobulin genes which are comprised of a variable region cDNA module plus a constant region which is composed in whole or in part of genomic sequences. Several human constant region genomic clones have been described (Ellison, J. W. et al., *Nucl. Acids Res.*, 10:4071 (1982), or Max, E. et al., *Cell*, 29:691 (1982)). The use of such genomic sequences may be convenient for the simultaneous introduction of immunoglobulin enhancers, splice signals, and transcription termination signals along with the constant region gene segment.

Different approaches can be followed to obtain complete $H_2L_2$ antibodies.

First, one can separately express the light and heavy chains followed by in vitro assembly of purified light and heavy chains into complete $H_2L_2$ IgG antibodies. The assembly pathways used for generation of complete $H_2L_2$ IgG molecules in cells have been extensively studied (see, for example, Scharff, M., *Harvey Lectures*, 69:125 (1974)). In vitro reaction parameters for the formation of IgG antibodies from reduced isolated light and heavy chains have been defined by Beychok, S., *Cells of Immunoglobulin Synthesis*, Academic Press, New York, page 69, 1979.

Second, it is possible to co-express light and heavy chains in the same cells to achieve intracellular association and linkage of heavy and light chains into complete $H_2L_2$ IgG antibodies. The co-expression can occur by using either the same or different plasmids in the same host.

POLYPEPTIDE PRODUCTS

The invention provides "chimeric" immunoglobulin chains, either heavy or light. A chimeric chain contains a constant region substantially similar to that present in of a natural human immunoglobulin, and a variable region having the desired antigenic specificity of the invention, i.e., to the specified human tumor antigen.

The invention also provides immunoglobulin molecules having heavy and light chains associated so that the overall molecule exhibits any desired binding and recognition properties. Various types of immunoglobulin molecules are provided: monovalent, divalent, molecules with chimeric heavy chains and non-chimeric light chains, or molecules with the invention's variable binding domains attached to moieties carrying desired functions.

Antibodies having chimeric heavy chains of the same or different variable region binding specificity and non-chimeric (i.e., all human or all non-human) light, chains, can be prepared by appropriate association of the needed polypeptide chains. These chains are individually prepared by the modular assembly methods of the invention.

USES

The antibodies of the invention having human constant region can be utilized for passive immunization, especially -in humans, without negative immune reactions such as serum sickness or anaphylactic shock. The antibodies can, of course, also be utilized in prior art immunodiagnostic assays and kits in detectably labelled form (e.g., enzymes, $^{125}I$, $^{14}C$, fluorescent labels, etc.), or in immobilized form (on polymeric tubes, beads, etc.), in labelled form for in vivo imaging, wherein the label can be a radioactive emitter, or an NMR contrasting agent such as a carbon-13 nucleus, or an X-ray contrasting agent, such as a heavy metal nucleus. The antibodies can also be used for in vitro localization of the antigen by appropriate labelling.

The antibodies can be used for therapeutic purposes, by themselves, in complement mediated lysis, or coupled to toxins or therapeutic moieties, such as ricin, etc.

Mixed antibody-enzyme molecules can be used for immunodiagnostic methods, such as ELISA. Mixed antibody-peptide effector conjugates can be used for targeted delivery of the effector moiety with a high degree of efficacy and specificity.

Specifically, the chimeric antibodies of this invention can be used for any and all uses in which the murine L6 monoclonal antibody can be used, with the obvious advantage that the chimeric ones are compatible with the human body.

Having now generally described the invention, the same will be further understood by reference to certain specific examples which are included herein for purposes of illustration only and are not intended to be limiting unless otherwise specified.

EXPERIMENTAL

Materials and Methods

Tissue Culture Cell Lines

The human cell lines GM2146 and GM1500 were obtained from the Human Mutant Cell Repository (Camden, New Jersey) and cultured in RPMI1640 plus 10% fetal bovine serum (M. A. Bioproducts). The cell line Sp2/0 was obtained from the American Type Culture Collection and grown in Dulbecco's Modified Eagle Medium (DMEM) plus 4.5 g/l glucose (M. A. Bioproducts) plus 10% fetal bovine serum (Hyclone, Sterile Systems, Logan, Utah). Media were supplemented with penicillin/streptomycin (Irvine Scientific, Irvine, California).

Recombinant Plasmid and Bacteriophage DNAs

The plasmids pBR322, pL1 and pUC12 were purchased from Pharmacia P-L Biochemicals (Milwaukee, Wisconsin). The plasmids pSV2-neo and pSV2-gpt were obtained from BRL (Gaithersburg, Maryland), and are available from the American Type Culture Collection (Rockville, Maryland). pHu-gamma-1 is a subclone of the 8.3 Kb HindIII to BamHI fragment of the human IgG1 chromosomal gene. An isolation method for the human IgG1 chromosomal gene is described by Ellison, J. W. et al., *Nucl. Acids Res.*, 10:4071 (1982). M8alphaRX12 contains the 0.7 Kb XbaI to EcoRI fragment containing the mouse heavy chain enhancer from the J-C intron region of the M603 chromosomal gene (Davis, M. et al., *Nature*, 283:733, 1979) inserted into M13mp10. DNA manipulations involving purification of plasmid DNA by buoyant density centrifugation, restriction endonuclease digestion, purification of DNA fragments by agarose gel electrophoresis, ligation and transformation of *E. coli* were as described by Maniatis, T. et al., *Molecular Cloning: A Laboratory Manual*, (1982) or other procedures. Restriction endonucleases and other DNA/RNA modifying enzymes were purchased from Boehringer-Mannheim (Indianapolis, Indiana), BRL, New England Biolabs (Beverly, Massachusetts) and Pharmacia P-L.

Oligonucleotide Preparation

Oligonucleotides were either synthesized by the triester method of Ito et al. (*Nucl. Acids Res.*, 10:1755 (1982)), or were purchased from ELESEN, Los Angeles, California. Tritylated, deblocked oligonucleotides were purified on Sephadex-G50, followed by reverse-phase HPLC with a 0–25% gradient of acetonitrile in 10 mM triethylamine-acetic acid, pH 7.2, on a C18 uBondapak column (Waters Associates). Detritylation was in 80% acetic acid for 30 min., followed by evaporation thrice. Oligonucleotides were labeled with [gamma-$^{32}$P]ATP plus T4 polynucleotide kinase.

RNA Preparation and Analysis

Total cellular RNA was prepared from tissue culture cells by the method of Auffray, C. and Rougeon, F. (*Eur. J. Biochem.*, 107:303 (1980)) or Chirgwin, J. M. et al. (*Biochemistry*, 18:5294 (1979)). Preparation of poly(A)+ RNA, methyl-mercury agarose gel electrophoresis, and "Northern" transfer to nitrocellulose were as described by Maniatis, T. et al., supra. Total cellular RNA or poly(A)+ RNA was directly bound to nitrocellulose by first treating the RNA with formaldehyde (White, B. A. and Bancroft, F. C., *J. Biol. Chem.*, 257:8569 (1982)). Hybridization to filterbound RNA was with nick-translated DNA fragments using conditions described by Margulies, D. H. et al. (*Nature*, 295:168 (1982)) or with $^{32}$P-labelled oligonucleotide using 4xSSC, 10X Denhardt's, 100 ug/ml salmon sperm DNA at 37° C. overnight, followed by washing in 4xSSC at 37° C.

cDNA Preparation and Cloning

Oligo-dT primed cDNA libraries were prepared from poly(A)+ RNA from GM1500 and GM2146 cells by the methods of Land, H. et al. (*Nucl. Acids Res.*, 9:2251 (1981)) and Gubler, V. and Hoffman, B. J., Gene, 25:263 (1983), respectively. The cDNA libraries were screened by hybridization (Maniatis, T., supra) with $^{32}$P-labelled oligonucleotides using the procedure of de Lange et al. (Cell, 34:891 (1983)), or with nick-translated DNA fragments.

Oligonucleotide Primer Extension and Cloning

Poly(A)+ RNA (20 ug) was mixed with 1.2 ug primer in 40 ul of 64 mM KCl. After denaturation at 90° C. for 5 min. and then chilling in ice, 3 units Human Placental Ribonuclease Inhibitor (BRL) was added in 3 ul of 1M Tris-HCl, pH 8.3. The oligonucleotide was annealed to the RNA at 42° C. for 15 minutes, then 12 ul of 0.05M DTT, 0.05M MgCl$_2$, and 1 mM each of dATP, dTTP, dCTP, and dGTP was added. 2 ul of alpha-$^{32}$P-dATP (400 Ci/mmol, New England Nuclear) was added, followed by 3 ul of AMV reverse transcriptase (19 units/ul, Life Sciences).

After incubation at 42° C. for 105 min., 2 ul 0.5M EDTA and 50 ul 10 mM Tris, 1 mM EDTA, pH 7.6 were added. Unincorporated nucleotides were removed by Sephadex G-50 spun column chromatography, and the RNA-DNA hybrid was extracted with phenol, then with chloroform, and precipitated with ethanol. Second strand synthesis, homopolymer tailing with dGTP or dCTP, and insertion into homopolymer tailed vectors was as described by Gubler and Hoffman, supra.

Site-Directed Mutagenesis

Single stranded M13 subclone DNA (1 ug) was combined with 20 ng oligonucleotide primer in 12.5 ul of Hin buffer (7 mM Tris-HCl, pH 7.6, 7 mM MgCl$_2$, 50 mM NaCl). After heating to 95° C. in a sealed tube, the primer was annealed to the template by slowly cooling from 70° C. to 37° C. for 90 minutes. 2 ul dNTPs (1 mM each), 1 ul $^{32}$P-dATP (10 uCi), 1 ul DTT (0.1M) and 0.4 ul Klenow DNA PolI (2u, Boehringer Mannheim) were added and chains extended at 37° C. for 30 minutes. To this was added 1 ul (10 ng) M13 reverse primer (New England Biolabs), and the heating/annealing and chain extension steps were repeated. The reaction was stopped with 2 ul of 0.5M EDTA, pH 8, plus 80 ul of 10 mM Tris-HCl, pH 7.6, 1 mM EDTA. The products were phenol extracted and purified by Sephadex G-50 spun column chromatography and ethanol precipitated prior to restriction enzyme digestion and ligation to the appropriate vector.

Transfection of Myeloma Tissue Culture Cells

The electroporation method of Potter, H. et al. (*Proc. Natl. Acad. Sci. U.S.A.*, 81:7161 (1984)) was used. After transfection, cells were allowed to recover in complete DMEM for 48–72 hours, then were seeded at 10,000 to 50,000 cells per well in 96-well culture plates in the presence of selective medium. G418 (GIBCO) selection was at 0.8 mg/ml, mycophenolic acid (Calbiochem) was at 6 ug/ml plus 0.25 mg/ml xanthine, and HAT (Sigma) was at the standard concentration.

Assays for Immunoglobulin Synthesis and Secretion

Secreted immunoglobulin was measured directly from tissue culture cell supernatants. Cytoplasmic protein extract was prepared by vortexing 106 cells in 160 ul of 1% NP40, 0.15M NaCl, 10 mM Tris, 1 mM EDTA, pH 7.6 and leaving the lysate at 0° C., 15 minutes, followed by centrifugation at 10,000×g to remove insoluble debris.

A double antibody sandwich ELISA (Voller, A. et al., in *Manual of Clinical Immunology*, 2nd Ed., Eds. Rose, N. and Friedman, H., pp. 359–371, 1980) using affinity purified antisera was used to detect specific immunoglobulins. For detection of human IgG, the plate-bound antiserum is goat anti-human IgG (KPL, Gaithersburg, Maryland) at 1/1000 dilution, while the peroxidase-bound antiserum is goat anti-human IgG (KPL or Tago, Burlingame) at 1/4000 dilution. For detection of human immunoglobulin kappa, the plate-bound antiserum is goat anti-human kappa (Tago) at 1/500 dilution, while the peroxidase-bound antiserum is goat anti-human kappa (Cappel) at 1/1000 dilution.

EXAMPLE 1

A Chimeric Mouse-Human Immunoglobulin with Cancer Antigen Specificity (1) Antibody L6

L6 monoclonal antibody (MAb) was obtained from a mouse which had been immunized with cells from a human lung carcinoma, after which spleen cells were hybridized with NS-1 mouse myeloma cells. The antibody binds to a previously not identified carbohydrate antigen which is expressed in large amounts at the surface of cells from most human carcinomas, including lung carcinomas (adeno, squamous), breast carcinomas, colon carcinomas and ovarian carcinomas, while the antigen is only present at trace levels in normal cells from the adult host. MAb L6 is an IgG2a and can mediate antibody dependent cellular cytotoxicity, ADCC, in the presence of human peripheral blood leukocytes as a source of effector cells, so as to lyse L6 positive tumor cells, and it can lyse L6 positive tumor cells in the presence of human serum as a source of complement; the lysis is detected as the release of $^{51}Cr$ from labelled cells over a 4 hour incubation period. MAb L6 can localize to L6 positive tumors xenotransplanted onto nude mice, and it can inhibit the outgrowth of such tumors. MAb L6 is described in Cancer Res. 46:3917–3923, 1986 (on MAb specificity) and in Proc. Natl. Acad. Sci. 83:7059–7063, 1986 (on MAb function). MAb L6 is also described in copending application Ser No. 776,321 filed Oct. 18, 1985, and now U.S. Pat. No. 4,906,562, and Ser. No. 684,759 filed Dec. 21, 1984, and now U.S. Pat. No. 4,935,495, the contents of each of which is fully incorporated by reference.

(2) Identification of J Sequences in the Immunoglobulin mRNA of L6

Frozen cells were thawed on ice for 10 minutes and then at room temperature. The suspension was diluted with 15 ml PBS and the cells were centrifuged down. They were resuspended, after washes in PBS, in 16 ml 3M LiCl, 6M urea and disrupted in a polytron shear. The preparation of mRNA and the selection of the poly(A+) fraction were carried out according to Auffray, C. and Rougeon, F., Eur. J. Biochem. 107:303, 1980.

The poly (A+) RNA from L6 was hybridized individually with labeled $J_H1$, $J_H2$, $J_H3$ and $J_H4$ oligonucleotides under conditions described by Nobrega et al. Anal. Biochem 131:141, 1983). The products were then subjected to electrophoresis in a 1.7% agarose-TBE gel. The gel was fixed in 10% TCA, blotted dry and exposed for autoradiography. The result showed that the L6 $v_H$ contains $J_H2$ sequences.

For the analysis of the $V_K$ mRNA, the dot-blot method of White and Bancroft J. Biol. Chem. 257:8569, (1982) was used. Poly (A+) RNA was immobilized on nitrocellulose filters and was hybridized to labeled probe-oligonucleotides at 40° in 4xSSC. These experiments show that L6 contains $JK^5$ sequences. A faint hybridization to $J_K2$ was observed.

(3) V Region cDNA Clones

A library primed by oligo (dT) on L6 poly (A+) RNA was screened for kappa clones with a mouse $C_K$ region probe. From the L6 library, several clones were isolated. A second screen with a 5' $J_K5$ specific probe identified the L6 ($J_K5$) light-chain clones. Heavy chain clones of L6 were isolated by screening with the $J_H2$ oligonucleotide.

The heavy and light chain genes or gene fragments from the cDNA clones, pH 3–6a and pL3–12a were inserted into M13 bacteriophage vectors for nucleotide sequence analysis. The complete nucleotide sequences of the variable region of these clones were determined (FIGS. 5A, 5B and 6) by the dideoxy chain termination method. These sequences predict V region amino acid compositions that agree well with the observed compositions, and predict peptide sequences which have been verified by direct amino acid sequencing of portions of the V regions.

The nucleotide sequences of the cDNA clones show that they are immunoglobulin V region clones as they contain amino acid residues diagnostic of V domains (Kabat et al. , Sequences of Proteins of Immunological Interest; U.S. Dept of HHS, 1983).

The L6 $V_H$ belongs to subgroup II. The cDNA predicts an N-terminal sequence of 24 amino acid residues identical to that of a known $V_H$(45–165 CRI; Margolies et al. Mol. Immunol. 18:1065, 1981). The L6 $V_H$ has the $J_H2$ sequence. The L6 $V_L$ is from the $V_K$-KpnI family (Nishi et al. Proc. Nat. Acd. Sci. U.S.A. 82:6399, 1985), and uses $J_K5$. The cloned L6 $V_L$ predicts an amino acid sequence which was confirmed by amino acid sequencing of peptides from the L6 light chain corresponding to residues 18–40 and 80–96.

(4) In Vitro Mutagenesis to Engineer Restriction Enzyme Sites in the J Region for Joining to a Human C-Module and to Remove Oligo (dC) Sequences 5' to the V Modules Both clones generated from priming with oligo (dT) L6 $V_K$ and L6 $V_H$ need to be modified. For the L6 $V_K$, the J-region mutagenesis primer JKHindIII, as shown in FIG. 6, was utilized. A human $C_K$ module derived from a cDNA clone was mutagenized to contain the HindIII sequence (see FIG. 4). The mutagenesis reaction was performed on M13 subclones of these genes. The frequency of mutant clones ranged from 0.5 to 1% of the plaques obtained.

It had been previously observed that the oligo (dC) sequence upstream of the AUG codon in a $V_H$ chimeric gene interferes with proper splicing in one particular gene construct. It was estimated that perhaps as much as 70% of the RNA transcripts had undergone the missplicing, wherein a cryptic 3' splice acceptor in the leader sequence was used. Therefore the oligo (dC) sequence upstream of the initiator AUG was removed in all of the clones.

In one approach, an oligonucleotide was used which contains a SalI restriction site to mutagenize the L6 $V_K$ clone. The primer used for this oligonucleotide-directed mutagenesis is a 22-mer which introduces a SalI site between the oligo (dC) and the initiator met codon (FIGS. 9A and 9B).

In a different approach, the nuclease BAL-31 was used to chew away the oligo (dC) in the L6 $V_H$ clone pH 3–6a. The size of the deletion in two of the mutants obtained was determined by nucleotide sequencing and is shown in FIGS. 7A and 7B. In both of these mutuants (delta 4 and delta 21), all of the oligo (dC) 5' to the coding region were deleted.

These clones were then modified by oligonucleotide-directed mutagenesis with the MJH2-ApaI primer (FIGS. 7A and 7B). This 31-base primer introduces an ApaI site in the mouse $C_H$ gene at a position analogous to an existing ApaI site in human Cgamma1 cDNA gene module. The primer introduces the appropriate codons for the human C gamma 1 gene. The chimeric heavy chain gene made by joining the mutagenized mouse $V_H$ gene module to a human $C_H$ module thus encodes a chimeric protein which contains no human amino acids for the entire $V_H$ region.

The human C gamma 1 gene module is a cDNA derived from GM2146 cells (Human Genetic Mutant Cell Repository, Newark, New Jersey). This C gamma 1 gene module was previously combined with a mouse $V_H$ gene module to form the chimeric expression plasmid pING2012E.

(5) L6 Chimeric Expression Plasmids

L6 chimeric heavy chain expression plasmids were derived from the replacement of the $V_H$ module pING2012E with the $V_H$ modules of mutants delta 21 and delta 4 to give the expression plasmids pING2111 and pING2112 (FIGS. 7A and 7B). These plasmids direct the synthesis of chimeric L6 heavy chain when transfected into mammalian cells.

For the L6 light chain chimeric gene, the SalI to HindIII fragment of the mouse $V_K$ module was joined to the human $C_K$ module by the procedure outlined in FIG. 8, forming pING2119. Replacement of the neo sequence with the *E. coli* gpt gene derived from pSV2-gpt resulted in pING2120, which expressed L6 chimeric light chain and confers mycophenolic acid resistance when transfected into mammalian cells.

The inclusion of both heavy and light chain chimeric genes in the same plasmid allows for the introduction into transfected cells of a 1:1 gene ratio of heavy and light chain genes leading to a balanced gene dosage. This may improve expression and decrease manipulations of transfected cells for optimal chimeric antibody expression. For this purpose, the DNA fragments derived from the chimeric heavy and light chain genes of pING2111 and pING2119 were combined into the expression plasmid pING2114 (FIGS. 9A and 9B). This expression plasmid contains a selectable $neo^R$ marker and separate transcription units for each chimeric gene, each including a mouse heavy chain enhancer.

The modifications and V-C joint regions of the L6 chimeric genes are summarized in FIG. 10.

(6) Stable Transfection of Mouse Lymphoid Cells for the Production of Chimeric Antibody Electroporation was used (Potter et al. supra; Toneguzzo et al. *Mol. Cell Biol.* 6:703 1986) for the introduction of L6 chimeric expression plasmid DNA into mouse Sp2/0 cells. The electroporation technique gave a transfection frequency of $1$–$10 \times 10^{-5}$ for the Sp2/0 cells.

The two gene expression plasmid pING2114 was linearized by digestion with AatII restriction endonuclease and transfected into Sp2/0 cells, giving approximately fifty G418 resistant clones which were screened for human heavy and light chain synthesis. The levels of chimeric antibody chain synthesis from two producers, D7 and 3E3, are shown in Table 1. Chimeric L6 antibody was prepared by culturing the D7 transfectant cells for 24 hours at $2 \times 10^6$ cells/ml in 5 l DMEM supplemented with HEPES buffer and penicillin and streptomycin. The supernatant was concentrated over an Areicon YM30 membrane in 10ram sodium phosphate buffer, pH 8.0. The preparation was loaded over a DEAE-Cellulose column, which separated the immunoglobulin into unbound and bound fractions. Samples from the DEAE-unbound, DEAE-bound and the pre--DEAE preparations (from 1.6 l of medium) was separately purified by affinity chromatography on a Protein-A Sepharose column, eluting with 0.1M sodium citrate pH 3.5. The eluted antibody was neutralized and concentrated by Amicon centricon filtration, in phosphate-buffered saline. The yields for the three preparations were 12 ug (DEAE unbound), 6 ug (DEAE bound), and 9 ug (pre-DEAE column). Western analysis of the antibody chains indicated that they were combined in an $H_2L_2$ tetramer like native immunoglobulins.

(7) Purification of Chimeric L6 Antibody Secreted in Tissue Culture a. Sp2/0.pING2114.D7 cells were grown in culture medium [DMEM (Gibco #320-1965), supplemented with 10% Fetal Bovine Serum (Hyclone #A-1111-D), 10 mM HEPES, 1× Glutamine-Pen-Strep (Irvine Scientific #9316) to $1 \times 10^6$ cell/ml.

b. The cells were then centrifuged at 400xg and resuspended in serum-free culture medium at $2 \times 10^6$ cell/ml for 18–24 hr.

c. The medium was centrifuged at 4000 RPM in a JS-4.2 rotor (3000xg) for 15 min.

d. 1.6 liter of supernatant was then filtered through a 0.45 micron filter and then concentrated over a YM30 (Amicon Corp.) filter to 25 ml.

e. The conductance of the concentrated supernatant was adjusted to 5.7–5.6 mS/cm CDM 80 radiometer and the pH was adjusted to 8.0.

f. The supernatant was centrifuged at 2000xg, 5 min., and then loaded onto a 40 ml DEAE column, which was preequilibrated with 10 mM sodium phosphate, pH 8.0.

g. The flow through fraction was collected and loaded onto a 1 ml protein A-Sepharose (Sigma) column preequilibrated with 10 mM sodium phosphate, pH 8.0.

h. The column was washed first with 6 ml 10 mM sodium phosphate buffer pH =8.0, followed by 8 ml 0.1M sodium citrate pH =3.5, then by 6 ml 0.1M citric acid (pH 2.2). Fractions of 0.5 ml were collected in tubes containing 50 ul 2M Tris base (Sigma).

i. The bulk of the IgG was in the pH 3.5 elution and was pooled and concentrated over Centricon 30 (Amicon Corp.) to approximately 0.06 ml.

j. The buffer was changed to PBS (10 mM sodium phosphate pH =7.4, 0.15M NaCl) in Centricon 30 by repeated diluting with PBS and reconcentrating.

k. The IgG solution was then adjusted to 0.10 ml and bovine serum albumin (Fraction V, U.S. Bio-chemicals) was added to 1.0% as a stabilizing reagent.

(8) Production in and Purification of Chimeric L6 Antibody from Ascites Fluid a. The ascites was first centrifuged at 2,000 xg for 10 min.

b. The conductance of the supernatant was adjusted to 5.7–5.6 mS/cm and its pH adjusted to 8.0.

c. Supernatant was then loaded onto a 40 ml DEAE-cellulose column pre-equilibrated with 10 mM $Na_2PO_4$ H pH 8.0.

d. The flow through from the DEAE column was collected and its pH was adjusted to 7.4, and the loaded onto a 1.0 ml goat anti-human IgG (H+L) -sepharose column.

e. The column was washed first with 6 ml of 10 mM sodium phosphate, 0.5M sodium chloride, followed by 8 ml of 0.5M $NH_4OH$, and 3M sodium thiocyanate.

f. The sodium thiocyanate eluate was pooled and dialyzed against 21 PBS overnight.

The antibody can be further concentrated by steps j. and k. of the previous procedure.

TABLE 1

| | Levels of Secreted Chimeric L6 Chains from Sp2/0 Transfectants[a] | | | | |
|---|---|---|---|---|---|
| | | Sp2/0.D7 | | Sp2/0.3E3 | |
| Culture Condition | FBS | Kappa[b] | Gamma[c] | Kappa[b] | Gamma[c] |
| 1. 20 ml, 2d, seed @ $2 \times 10^5$/ml | + | 17 | 77 | 100 | 700 |
| 2. 200 ml, 2d, seed @ $2.5 \times 10^5$/ml | + | 0.9 | 6 | 80 | 215 |
| 3. 200 ml, 1d, seed @ | − | 1.9 | 3.8 | 97 | 221 |

TABLE 1-continued

Levels of Secreted Chimeric L6
Chains from Sp2/0 Transfectants[a]

| | | Sp2/0.D7 | | Sp2/0.3E3 | |
|---|---|---|---|---|---|
| Culture Condition | FBS | Kappa[b] | Gamma[c] | Kappa[b] | Gamma[c] |
| 2 × 10⁶/ml 4. Balb/c ascites | — | 5,160 | 19,170 | ND | ND |

[a]Sp2/0 cells transfected by electroporation with pING2114(pL6HL)
[b]ug/l measured by ELISA specific for human Kappa - human Bence-Jones protein standard.
[c]ug/l measured by ELISA specific for human gamma - human IgG standard.
ND - Not determined.
FBS: Fetal Bovine Serum (9) Studies Performed on the Chimeric L6 Anti-body First, the samples were tested with a binding assay, in which cells of both an L6 antigen-positive and an L6 antigen-negative cell line were incubated with standard mouse monoclonal antibody L6, chimeric L6 antibody derived from the cell culture supernatants, and chimeric L6 antibody derived from ascites (as previously described) followed by a second reagent, fluorescein-isothiocyanate (FITC) -conjugated goat antibodies to human (or mouse, for the standard) immunoglobulin.

Since the binding assay showed strong reactivity of the chimeric L6 on the L6 antigen positive cell line and total lack of reactivity on the negative cell line, the next step was to test for the ability of the chimeric L6 to inhibit the binding of mouse L6 to antigen positive cells; such inhibition assays are used routinely to establish the identity of two antibodies' recognition of antigen. These data are discussed below ("Inhibition of binding"). As part of these studies, a rough estimate of antibody avidity was made.

Finally, two aspects of antibody function were studied, the ability to mediate ADCC in the presence of human peripheral blood leukocytes, and the ability to kill L6 positive tumor cells in the presence of human serum as a source of complement (see "Functional Assays" below).

Binding Assays. Cells from a human colon carcinoma line, 3347, which had been previously shown to express approximately $5 \times 10^5$ molecules of the L6 antigen at the cell surface, were used as targets. Cells from the T cell line HSB2 was used as a negative control, since they, according to previous testing, do not express detectable amounts of the L6 antigen. The target cells were first incubated for 30 min at 4° C. with either the chimeric L6 or with mouse L6 standard, which had been purified from mouse ascites. This was followed by incubation with a second, FITC-labelled, reagent, which for the chimeric antibody was goat- anti-human immunoglobulin, obtained from TAGO (Burlingame, CA), and used at a dilution of 1:50. For the mouse standard, it was goat-anti-mouse immunoglobulin, also obtained from TAGO and used at a dilution of 1:50. Antibody binding to the cell surface was determined using a Coulter Model EPIC-C cell sorter.

As shown in Table 2 and Table 2A, both the chimeric and the mouse standard L6 bound significantly, and to approximately the same extent, to the L6 positive 3347 line. They did not bind above background to the L6 negative HSB2 line.

In view of the fact that the three different chimeric L6 samples presented in Table 2 behaved similarly in the binding assays, they were pooled for the inhibition studies presented below. The same inhibition studies were performed for chimeric L6 derived from ascites fluid presented in Table 2A.

Inhibition of Binding. As the next step was studied the extent to which graded doses of the chimeric L6 antibody, or the standard mouse L6, could inhibit the binding of an FITC-labelled mouse L6 to the surface of antigen positive 3347 colon carcinoma cells.

Both the chimeric and mouse standard L6 inhibited the binding of the directly labelled L6 antibody, with the binding curves being parallel. The chimeric antibody was slightly less effective than the standard, as indicated by the results which showed that 3.4 ug/ml of the pooled chimeric L6MAb, as compared to 2.0 ug/ml of the standard mouse L6MAb was needed for 50% inhibition of the binding, and that 5.5 ug/ml of the chimeric L6 (derived from ascites) as compared to 2.7 Ug/ml of the standard mouse L6MAb was needed for 50% inhibition of binding.

As part of these studies, a rough estimate was made of antibody avidity. The avidity of the standard mouse L6 had been previously determined to be approximately $4 \times 10^8$ The data indicated that there were no significant differences in avidity between the chimeric and the mouse L6.

Functional Assays. A comparison was made between the ability of the chimeric L6 and standard mouse L6 to lyse L6 antigen positive cells in the presence of human peripheral blood leukocytes as a source of effector cells (mediating Antibody Dependent Cellular Cytotoxcity, ADCC) or human serum as a source of complement (mediating Complement-Dependent Cytolysis, CDC).

As shown in Table 3 and Tables 3A–3D, the chimeric L6 was superior to the simultaneously tested sample of mouse L6 in causing ADCC, as measured by a 4 hr $^{51}$Cr release test.

Tables 4 and 4A–4B present the data from studies on complement-mediated target cell lysis. In this case, a high cytolytic activity was observed with both the mouse and the chimeric L6 antibodies.

CONCLUSIONS

The results presented above demonstrate a number of important unexpected qualities of the chimeric L6 monoclonal antibody of the invention. Firstly, the chimeric L6 antibody binds to L6 antigen positive tumor cells to approximately the same extent as the mouse L6 standard and with approximately the same avidity. This is significant for the following reasons: the L6 antibody defines (a) a surface carbohydrate antigen, and (b) a protein antigen of about 20,000 daltons, each of which is characteristic of non-small cell lung carcinoma (NSCLC) and certain other human carcinomas. Significantly, the L6 antibody does not bind detectably to normal cells such as fibroblasts, endothelial cells, or epithelial cells in the major organs. Thus the chimeric L6 monoclonal antibody defines an antigen that is specific for carcinoma cells and not normal cells.

In addition to the ability of the chimeric L6 monoclonal antibodies of the present invention to bind specifically to malignant cells and localize tumors, the chimeric L6 exerts profound biological effects upon binding to its target, which make the chimeric antibody a prime candidate for tumor immunotherapy. The results presented herein demonstrate that chimeric L6 is capable of binding to tumor cells and upon binding kills the tumor cells, either by ADCC or CDC. Such tumor killing activity was demonstrated using concentrations of chimeric L6 antibody as low as 0.01 ug/ml (10 ng/ml).

Although the prospect of attempting tumor therapy using monoclonal antibodies is attractive, with some partial tumor regressions being reported, to date such monoclonal antibody therapy has been met with limited success (Houghton, February 1985, Proc. Natl. Acad. Sci. 82:1242–1246) The therapeutic efficacy of mouse monoclonal antibodies (which are the ones that have been tried so far) appears to be too low for most practical purposes. The discovery of the profound biological activity of chimeric L6 coupled with its specificity for a carcinoma antigen makes the chimeric L6 antibody a choice therapeutic agent for the treatment of tumors in vivo. Moreover, because of the "human" properties which will make the chimeric L6 monoclonal antibodies more resistant to clearance in vivo, the chimeric L6 monoclonal antibodies will be advantageously used not only for therapy with unmodified chimeric antibodies, but also for development of various immunoconjugates with drugs, toxins, immunomodulators, isotopes, etc., as well as for diagnostic purposes such as in vivo imaging of tumors using appropriately labelled chimeric L6 antibodies. Such immunoconjugation techniques are known to those skilled in the art and can be used to modify the chimeric L6 antibody molecules of the present invention.

Two illustrative cell lines secreting chimeric L6 antibody were deposited prior to the U.S. filing date at the ATCC, Rockville Maryland. These are transfected hybridoma C255 (corresponds to 3E3 cells upra) ATCC HB 9240 and transfected hybridoma C256 (D7 cells supra) ATCC HB 9241.

(10) Expression in Yeast of L6 Chains

Genetic sequences coding for Chimeric L6 antibody heavy and light chains were prepared and introduced into vectors. Yeast cells were transformed therewith and expression of separate heavy and light antibody chains for L6 antibody was detected.

The present invention is not to be limited in scope by the cell lines deposited since the deposited embodiment is intended as a single illustration of one aspect of the invention and all cell lines which are functionally equivalent are within the scope of the invention. Indeed, various modifications of the invention in addition to those shown in the art from the foregoing description and accompanying drawings. Such modifications are intended to fall within the scope of the appended claims.

TABLE 2

Binding Assays Of Chimeric L6 Antibody and Mouse L6 Monoclonal Antibody on an L6 Antigen Positive and L6 Antigen Negative Cell Line.

| Antibody | Batch | GAM | GAH |
|---|---|---|---|
| | | Binding Ratio For* H3347 Cells (L6 +) | |
| Standard L6 | | 56.6 | 4.2 |
| Chimeric L6 | a | 1.3 | 110.3 |
| | b | 1.3 | 110.3 |
| | c | 1.3 | 110.3 |
| | | Binding Ratio For* HSB-2 Cells (L6 −) | |
| Standard L6 | | 1.1 | 1.1 |
| Chimeric L6 | a | 1.0 | 1.0 |
| | b | 1.0 | 1.1 |
| | c | 1.0 | 1.1 |

*All assays were conducted using an antibody concentration of 10 ug/ml. The binding ratio is the number of times brighter a test sample is than a control sample treated with GAM (FITC conjugated goat-anti-mouse) or GAH (FITC conjugated goat anti-human) alone. A ratio of 1 means that the test sample is just as bright as the control; a ratio of 2 means the test sample is twice as bright as the control, etc.

TABLE 2A

Binding Assays Of Chimeric L6 Antibody and Mouse Monoclonal Antibody on an L6 Antigen Positive and L6 Antigen Negative Cell Line.

| Antibody | Antibody Concentration (ug/ml) | GAM | GAH |
|---|---|---|---|
| | | Binding Ratio For* H3347 Cells (L6 +) | |
| Standard L6 | 30 | 38 | 4 |
| | 10 | 49 | 4 |
| | 3 | 40 | 3 |
| Chimeric L6 (Ascites) | 30 | 2 | 108 |
| | 10 | 2 | 84 |
| | 3 | 1 | 42 |
| Chimeric L6 (Cell Culture) | 30 | 1 | 105 |
| | 10 | 1 | 86 |
| | 3 | 1 | 44 |
| | | Binding Ratio For** HSB-2 Cells (L6 −) | |
| Standard L6 | 10 | 1 | 1 |
| Chimeric L6 (Ascites) | 10 | 1 | 1 |
| Chimeric L6 (Cell Culture) | 10 | 1 | 1 |

*The binding ratio is the number of times brighter a test sample is than a control sample treated with GAM (FITC conjugated goat anti-human) alone. A ratio of 1 means that the test sample is just as bright as the control; a ratio of 2 means the test sample is twice as bright as the control, etc.

TABLE 3

ADCC of Chimeric L6 (Mouse) L6 Antibodies On Colon Carcinoma Cell Line C3347.

| Antibody | Antibody Concentration (ug/ml) | PBL per Target Cell | % Cytolysis* |
|---|---|---|---|
| Chimeric L6 (Cell Culture) | 10 | 100 | 64 |
| | 5 | 100 | 70 |
| | 10 | 0 | 2 |
| Standard L6 | 10 | 100 | 24 |
| | 5 | 100 | 17 |
| | 10 | 0 | 2 |
| None | 0 | 100 | 1 |

*The target cells had been labelled with $^{51}$Cr and were exposed for 4 hours to a combination of MAb and human peripheral blood leukocytes (PBL), and the release of $^{51}$Cr was measured subsequently. The release of $^{51}$Cr (after corrections of values for spontaneous release from untreated cells) is a measure of the percent cytolsis.

TABLE 3A

ADCC of Chimeric L6 and Standard (Mouse) L6 Antibodies On Colon Carcinoma Cell Line C3347.

| Antibody | Antibody Concentration (ug/ml) | PBL per Target Cell | % Cytolysis* |
|---|---|---|---|
| Chimeric L6 (Ascites) | 20 | 100 | 80 |
| | 10 | 100 | 74 |
| | 5 | 100 | 71 |
| | 2.5 | 100 | 71 |
| | 20 | 0 | 0 |
| Chimeric L6 (Cell Culture) | 10 | 100 | 84 |
| | 5 | 100 | 74 |
| | 2.5 | 100 | 67 |
| | 10 | 0 | 3 |
| Standard L6 | 20 | 100 | 32 |
| | 10 | 100 | 26 |
| | 20 | 0 | 0 |

*The target cells had been labelled with $^{51}$Cr and were exposed for 4 hours to a combination of MAb and human peripheral blood leukocytes (PBL), and the release of $^{51}$Cr was measured subsequently. The release of $^{51}$Cr (after corrections of values for spontaneous release from untreated cells) is a measure of the percent cytolsis.

TABLE 3B

ADCC of Chimeric L6 and Standard (Mouse) L6 Antibodies On Colon Carcinoma Cell Line C3347.

| Antibody | Antibody Concentration (ug/ml) | PBL per Target Cell | % Cytolysis* |
|---|---|---|---|
| Chimeric L6 | 5 | 100 | 84 |
| (Ascites) | 2.5 | 100 | 78 |
|  | 1.25 | 100 | 85 |
|  | 0.63 | 100 | 81 |
|  | 0.31 | 100 | 80 |
|  | 0.16 | 100 | 71 |
|  | 0.08 | 100 | 65 |
|  | 5 | 0 | 0 |
| Standard L6 | 5 | 100 | 32 |
|  | 5 | 0 | 0 |
| None | 0 | 100 | 19 |

*The target cells had been labelled with $^{51}$Cr and were exposed for 4 hours to a combination of MAb and human peripheral blood leukocytes (PBL), and the release of $^{51}$Cr was measured subsequently. The release of $^{51}$Cr (after corrections of values for spontaneous release from untreated cells) is a measure of the percent cytolsis.

TABLE 3C

ADCC of Chimeric L6 and Standard (Mouse) L6 Antibodies On Melanoma Cell Line M2669.

| Antibody | Antibody Concentration (ug/ml) | PBL per Target Cell | % Cytolysis* |
|---|---|---|---|
| Chimeric L6 | 10 | 100 | 35 |
| (Ascites) | 1 | 100 | 31 |
|  | 0.1 | 100 | 27 |
|  | 0.01 | 100 | 15 |
|  | 0.001 | 100 | 13 |
|  | 0.0001 | 100 | 0 |
|  |  |  | 15 |
| Standard L6 | 10 | 100 | 9 |
|  | 1 | 100 | 15 |
| None | 0 | 100 | 9 |
| Chimeric L6 | 10 | 10 | 19 |
| (Ascites) | 1 | 10 | 15 |
|  | 0.1 | 10 | 11 |
|  | 0.01 | 10 | 13 |
|  | 0.001 | 10 | 22 |
|  | 0.0001 | 10 | 11 |
| Standard L6 | 10 | 10 | 7 |
|  | 1 | 10 | 6 |
| None | 0 | 10 | 8 |
| Chimeric L6 | 10 | 0 | 4 |
| (Ascites) |  |  |  |
| Standard L6 | 10 | 0 | 9 |

*The target cells had been labelled with $^{51}$Cr and were exposed for 4 hours to a combination of MAb and Human peripheral blood leukocytes (PBL), and the release of $^{51}$Cr was measured subsequently. The release of $^{51}$Cr (after corrections of values for spontaneous release from untreated cells) is a measure of the percent cytolysis.

TABLE 3D

ADCC of Chimeric L6 and Standard (Mouse) L6 Antibodies On Colon Carcinoma Cell Line C3347.

| Antibody | Antibody Concentration (ug/ml) | PBL per Target Cell | % Cytolysis* |
|---|---|---|---|
| Chimeric L6 | 10 | 100 | 62 |
| (Ascites) | 1 | 100 | 66 |
|  | 0.1 | 100 | 69 |
|  | 0.01 | 100 | 26 |
|  | 0.001 | 100 | 8 |
|  | 0.0001 | 100 | 3 |
|  | 10 | 0 | 0 |
| Standard L6 | 10 | 100 | 19 |
|  | 1 | 100 | 24 |
|  |  | 0 | 0 |
| None | 0 | 100 | 8 |

*The target cells had been labelled with $^{51}$Cr and were exposed for 4 hours to a combination of MAb and Human peripheral blood leukocytes (PBL), and the release of $^{51}$Cr (after corrections of values for spontaneous release from untreated cells) is a measure of the percent cytolysis.

TABLE 4

Complement-dependent cytotoxic effect of chimeric and standard (mouse) L6 on colon carcinoma cells from line 3347, as measured by a 4-hr $^{51}$Cr-release assay. Human serum from a healthy subject was used as the source of complement.

| Antibody | Human complement | % Cytolysis |
|---|---|---|
| L6 Standard 10 ug/ml | Yes | 90 |
| L6 chimeric 10 ug/ml | Yes | 89 |
| L6 Standard 10 ug/ml | No | 0 |
| L6 chimeric 10 ug/ml | No | 1 |

TABLE 4A

Complement Dependent Cytotoxic Effect of Chimeric L6 and Standard (Mouse) L6 Antibodies on Colon Carcinoma Cell Line C3347

| Antibody | Antibody Concentration (ug/ml) | Human Complement | % Cytolysis* |
|---|---|---|---|
| Chimeric L6 | 20 | + | 29 |
| (Ascites) | 10 | + | 23 |
|  | 5 | + | 18 |
|  | 2.5 | + | 8 |
|  | 20 | Inactivated | 0 |
|  | 10 | 0 | 0 |
| Chimeric L6 | 20 | + | 29 |
| (Cell Culture)) | 5 | + | 26 |
|  | 2.5 | + | 18 |
|  | 20 | Inactivated | 0 |
|  | 10 | 0 | 4 |
| Standard L6 | 20 | + | 55 |
|  | 10 | + | 37 |
|  | 20 | Inactivated | 0 |
|  | 20 | 0 | 1 |
| None | 0 | + | 0 |

*Complement mediated cytolysis was measured by a 4 hour $^{51}$Cr-release assay. Human serum from a healthy subject was used as the source of complement.

TABLE 4B

Complement Dependent Cytotoxic Effect of Chimeric L6 and Standard (Mouse) L6 Antibodies on Colon Carcinoma Cell Line C3347

| Antibody | Antibody Concentration (ug/ml) | Human Complement | % Cytolysis* |
|---|---|---|---|
| Chimeric L6 | 10 | + | 209 |
| (Ascites) | 5 | + | 155 |
|  | 2.5 | + | 166 |
|  | 1.25 | + | 114 |
|  | 0.6 | + | 63 |
|  | 0.3 | + | 17 |
|  | 10 | 0 | 0 |
| Standard L6 | 10 | + | 96 |
|  | 5 | + | 83 |
|  | 2.5 | + | 48 |
|  | 1.25 | + | 18 |
|  | 0.6 | + | 7 |
|  | 0.3 | + | 4 |
|  | 10 | 0 | 2 |
| None | 0 | + | 0 |

*Complement mediated cytolysis was measured by a 4 hour $^{51}$Cr-release assay. Human serum from a healthy subject was used as the source of complement.

What is new and intended to be covered by Letters Patent of the United States is:

1. A chimeric antibody specific for the L6 human tumor antigen, comprising a human constant region and a variable region which are produced by transfected eukaryotic cells, in which:
   (a) the antigen combining site of the chimeric antibody competitively inhibits the immunospecific binding of monoclonal antibody L6 produced by hybridoma HB8677 as deposited with the ATCC, and (b) the chimeric antibody mediates a more potent antibody-dependent cellular cytotoxicity than that mediated by monoclonal antibody L6 produced by hybrodoma HB8677 as deposited with the ATCC.

2. A chimeric antibody specific for the L6 human tumor antigen, comprising a human constant region and a murine variable region which are produced by transfected eukaryotic cells, in which:

(a) the antigen combining site of the chimeric antibody competitively inhibits the immunospecific binding of monoclonal antibody L6 produced by hydridoma HB8677 as deposited with the ATCC, and (b) the chimeric antibody mediates a more potent antibody-dependent cellular cytotoxicity than that mediated by monoclonal antibody L6 produced by hybridoma HB8677 as deposited with the ATCC.

3. A chimeric antibody specific for the L6 human tumor antigen produced by hybridoma HB9240 as deposited with the ATCC.

4. A chimeric antibody specific for the L6 human tumor antigen produced by hybridoma HB9241 as deposited with the ATCC.

* * * * *